United States Patent
Richey et al.

(12)

(10) Patent No.: US 10,799,478 B2
(45) Date of Patent: Oct. 13, 2020

(54) TREATMENT OF ANDROGEN DEPRIVATION THERAPY ASSOCIATED SYMPTOMS

(71) Applicant: Eli Lilly and Company, Indianapolis, IN (US)

(72) Inventors: Rachel Nicole Richey, Indianapolis, IN (US); Hannah Yu, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/216,256

(22) Filed: Dec. 11, 2018

(65) Prior Publication Data

US 2019/0111039 A1     Apr. 18, 2019

Related U.S. Application Data

(62) Division of application No. 15/327,054, filed as application No. PCT/US2015/048801 on Sep. 8, 2015.

(Continued)

(51) Int. Cl.
*A61K 31/403* (2006.01)
*C07D 401/06* (2006.01)
(Continued)

(52) U.S. Cl.
CPC ........ *A61K 31/403* (2013.01); *A61K 31/4439* (2013.01); *C07D 209/60* (2013.01); *C07D 209/94* (2013.01); *C07D 401/06* (2013.01)

(58) Field of Classification Search
CPC ........................ A61K 31/403; C07D 209/60
(Continued)

(56) References Cited

U.S. PATENT DOCUMENTS 7,968,587 B2 * 6/2011 Gavardinas .......... C07D 209/58
                                                                514/411
8,110,562 B2   2/2012 Dalton
(Continued)

FOREIGN PATENT DOCUMENTS

WO   WO 2008/063867   5/2008
WO   WO 2009/027746   3/2009
(Continued)

OTHER PUBLICATIONS

Wenqing Gao, et al., "Selective Androgen Receptor Modulator Treatment Improves Muscle Strength and Body Composition and Prevents Bone Loss in Orchidectomized Rats," Endocrinology, vol. 146, No. 11, pp. 4887-4897, Nov. 1, 2005, XP055226511.

(Continued)

*Primary Examiner* — Craig D Ricci
*Assistant Examiner* — Janet L. Coppins
(74) *Attorney, Agent, or Firm* — Mark S. Cohen; Pearl Cohen; Zedek Latzer Baratz LLP

(57) ABSTRACT

The present invention provides a method of treating symptoms associated with Androgen Deprivation Therapy comprising administering to a patient in need of such treatment an effective amount of a compound of Formula I:

(Continued)

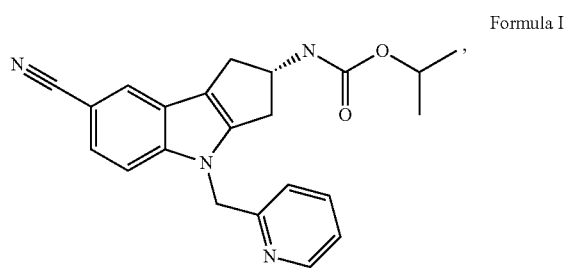

Formula I or a pharmaceutically acceptable salt thereof.

7 Claims, 11 Drawing Sheets

Related U.S. Application Data

(60) Provisional application No. 62/049,192, filed on Sep. 11, 2014.

(51) Int. Cl.
  C07D 209/94 (2006.01)
  C07D 209/60 (2006.01)
  A61K 31/4439 (2006.01)

(58) Field of Classification Search
  USPC .......................................................... 514/411
  See application file for complete search history.

(56) References Cited

U.S. PATENT DOCUMENTS

| 8,183,388 | B2 * | 5/2012 | Jadhav | C07D 405/06 548/449 |
|---|---|---|---|---|
| 2007/0281977 | A1 | 12/2007 | Calderon et al. | |
| 2008/0080143 | A1 | 4/2008 | Peng et al. | |
| 2009/0143344 | A1 | 6/2009 | Chang | |
| 2010/0069404 | A1 | 3/2010 | Gavardinas et al. | |
| 2011/0118326 | A1 | 5/2011 | Jadhav et al. | |
| 2014/0134274 | A1 | 5/2014 | Steiner | |
| 2015/0299189 | A1 | 10/2015 | Tanaka et al. | |

FOREIGN PATENT DOCUMENTS

| WO | WO 2009/082437 | 7/2009 |
| WO | WO 2011/060019 | 5/2011 |
| WO | WO 2012/139093 | 10/2012 |

OTHER PUBLICATIONS

Rohayem J. et al., "Androgen deprivation therapy in prostate cancer; Indication and systemic consequences; Antiandrogene Therapie des Prostatakarzinoms; Indikation und systemische Folgen," Der Urologe, Ausgabe A; Zeitschrift Fur Klinische Und Praktische Urologie Organ Der Deutschen Gesellschaft Fur Urologie, Springer, Berlin, DE, vol. 51, No. 4, pp. 557-566; Apr. 5, 2012, XP035040241.
P. Yi et al., "Disposition and Metabolism of LY2452473, a Selective Androgen Receptor Modulator, in Humans," Drug Metabolism and Disposition, vol. 40, No. 12, pp. 2354-2364, Sep. 7, 2012, XP055226399.
Anonymous: "NCT02499497 on Jul. 15, 2015, ClinicalTrials.gov Archive," XP055226402.
Narayanan Ramesh et al: "Selective androgen receptor modulators in preclinical and clinical development", Nuclear Receptor Signaling: NRS, Bethesda, MD.: Pubmed Central, US, vol. 6, Nov. 26, 2008 (Nov. 26, 2008), pp. EOI 0-1 , XP002623904, ISSN: 1550-7629, DOI: 10.1621/NRS.06010.
Suzman et al, "Does Degree of Androgen Suppression Matter in Hormone-Sensitive Prostate Cancer?" Journal of Clinical Oncology, Apr. 1, 2015, vol. 33, No. 10, 1098-1 100, DOI: 10.1200/J CO.201 4.60.1419.
Decision of the Intellectual Property Office of ROC (Taiwan) dated Dec. 7, 2016 regarding TW Application 104127732 (English Translation).
Search Report dated May 19, 2016 regarding TW Application 104127732 (English Translation).
Japanese Patent Office Notice of Reason for Rejection dated Dec. 5, 2017 regarding JP Application 2017-513539 (English Translation).
Office Action, dated Apr. 25, 2018, from corresponding Korean Patent Application No. 10-2017-7006425.
Office Action, dated Aug. 21, 2018, from corresponding Ukrainian Patent Application No. a201701774.
Office Action, dated Aug. 23, 2018, from corresponding Chinese Patent Application No. 201580048887.4.
Office Action, dated Feb. 21, 2019 from corresponding Australian Patent Application No. 2018202714.
Office Action, dated Jul. 24, 2018, from corresponding Japanese Patent Application No. 2017-513539.
Office Action, dated Jul. 9, 2018, from corresponding Korean Patent Application No. 10-2017-7006425.
Office Action, dated Jun. 26, 2018, from corresponding Canadian Patent Application No. 2,956,514.
Office Action, dated May 23, 2018, from corresponding Korean Patent Application No. 10-2018-7010670.
Office Action, dated May 3, 2018, from corresponding Eurasian Patent Application No. 201790220.
Office Action, dated Oct. 24, 2018, from corresponding Eurasian Patent Application No. 201891008.
Office Action, dated Oct. 25, 2018, from corresponding Korean Patent Application No. 10-2017-7006425.
Rohayem J., et al., "Androgen Deprivation Therapy in Prostrate Cancer; Indication and Systemic Consequences; Antiandrogene Therapie des Prostatakarzinoms; Indikation und Systemische Folgen, "Der Urologe, Ausgabe A.; Zeitschrift Fur Klinische und Prakitsche Urologie Organ Der Deutschen Gesellschaft Fur Urologie, Springer, Berlin, DE, vol. 40, No. 12, pp. 2354-2364, Sep. 7, 2012, XP05226399.
Written Opinion from Singapore Appl. No. 11201701630V dated Apr. 4, 2019.
PCT International Preliminary Report on Patentability regarding PCT Application No. PCT/US2015/048801 dated Dec. 21, 2016.
PCT Written Opinion of the International Searching Authority regarding PCT Application No. PCT/US2015/048801 dated Mar. 17, 2016.

* cited by examiner

TREATMENT OF ANDROGEN DEPRIVATION THERAPY ASSOCIATED SYMPTOMS

CROSS REFERENCE TO RELATED APPLICATIONS

This application is a divisional of U.S. patent application Ser. No. 15/327,054, filed Jan. 18, 2017, which is a National Phase Application of PCT International Application No. PCT/US2015/048801, filed on Sep. 8, 2015, which claims the benefit of U.S. Provisional Application Ser. No. 62/049,192, filed Sep. 11, 2014.

BACKGROUND OF THE INVENTION

The present invention relates to the treatment of Androgen Deprivation Therapy associated symptoms using (S)-(7-cyano-4-pyridin-2-ylmethyl-1,2,3,4-tetrahydro-cyclopenta[b]indol-2-yl)-carbamic acid isopropyl ester, or a pharmaceutically acceptable salt thereof.

The present invention is in the field of treatment of symptoms associated with Androgen Deprivation Therapy. Androgen Deprivation Therapy (ADT) or androgen suppression therapy is a common therapy used to decrease the aggressiveness of prostate cancer in conjunction with other therapeutic options focused on the eradication of the cancer. During ADT, the levels of androgens, or male hormones, are reduced in the body to prevent them from reaching prostate cancer cells. Androgens, such as testosterone and dihydrotestosterone (DHT), stimulate the growth of prostate cancer cells. However, it has been discovered that prostate cancers may grow more slowly or even shrink if androgen levels are lowered. In the United States, it is estimated that approximately one third of prostate cancer patients will have received ADT at some point during the treatment of their disease.

There are several treatment options available to lower androgen levels, such as orchiectomy or surgical castration, luteinizing hormone-relasing hormone (LHRH) analogs, such as leuprolide (marketed in the United States as Lupron®, Eligard®), goserelin (marketed in the United States as Zoladex®), triptorelin (marketed in the United States as Trelstar®), and histrelin (marketed in the United States as Vantas®), and LHRH antagonists, such as degarelix (marketed in the United States as Firmagon®) and abiraterone (marketed in the United States as Zytiga®).

Most men with advanced prostate cancer respond well to ADT. ADT is typically indicated when prostate cancers extend beyond the prostate capsule based upon clinical staging (T3 disease), when first line in metastatic prostate cancer with GnRH agonists/antagonists or chemical castration.

There are potential side effects associated with hormone therapy which can have detrimental effects on quality of life and increase the risks of patient discontinuation of the ADT therapy. For example, the side effects can include reduced or absent libido, erectile dysfunction, shrinking of the male sexual organs, hot flashes, osteoporosis, anemia, reduced muscle mass, decreased muscle strength, increase in body fat, and weight gain, due to the changes in the levels of the hormones testosterone and estrogen. Current treatments for the side effects associated with ADT are known in the art. See US 2009/0143344 (hot flashes—5HT2A or D2R antagonist); US 2007/0281977 (hot flashes—muscarinic receptor antagonist); US 2008/0080143 (osteoporosis, bone fractures, loss of BMD, hot flashes gynochornastia hair loss—torimifene). However, there remains a need in the art for alternate therapies wherein certain side effects of ADT may be reduced. In fact, until recently, intermittent androgen deprivation (IAD) was recommended to attempt to minimize the adverse effects of medical castration by withdrawing treatment in patients who have responded to ADT and then reinstituting ADT when there is evidence of recurrent or progressive disease. However, a trial of 1749 patients randomized to continuous ADT versus IAD for a median follow-up of 9.8 years demonstrated that continuous ADT is superior to IAD. A therapy to improve tolerability of the side effects of ADT could lead to improvements in compliance and result in better outcomes to patients.

Selective androgen receptor modulators (SARMs) have been found to display a differentiated profile of activity in androgenic tissues. In particular, such agents preferably display androgen agonist activity in anabolic tissues such as muscle or bone, yet are only partial agonists or even antagonists in other androgenic tissues such as the prostate or seminal vesicles. Thus, the use of an androgen receptor (AR) modulator may alleviate the symptoms of ADT for prostate cancer patients.

DETAILED DESCRIPTION OF THE INVENTION

Figure 1:
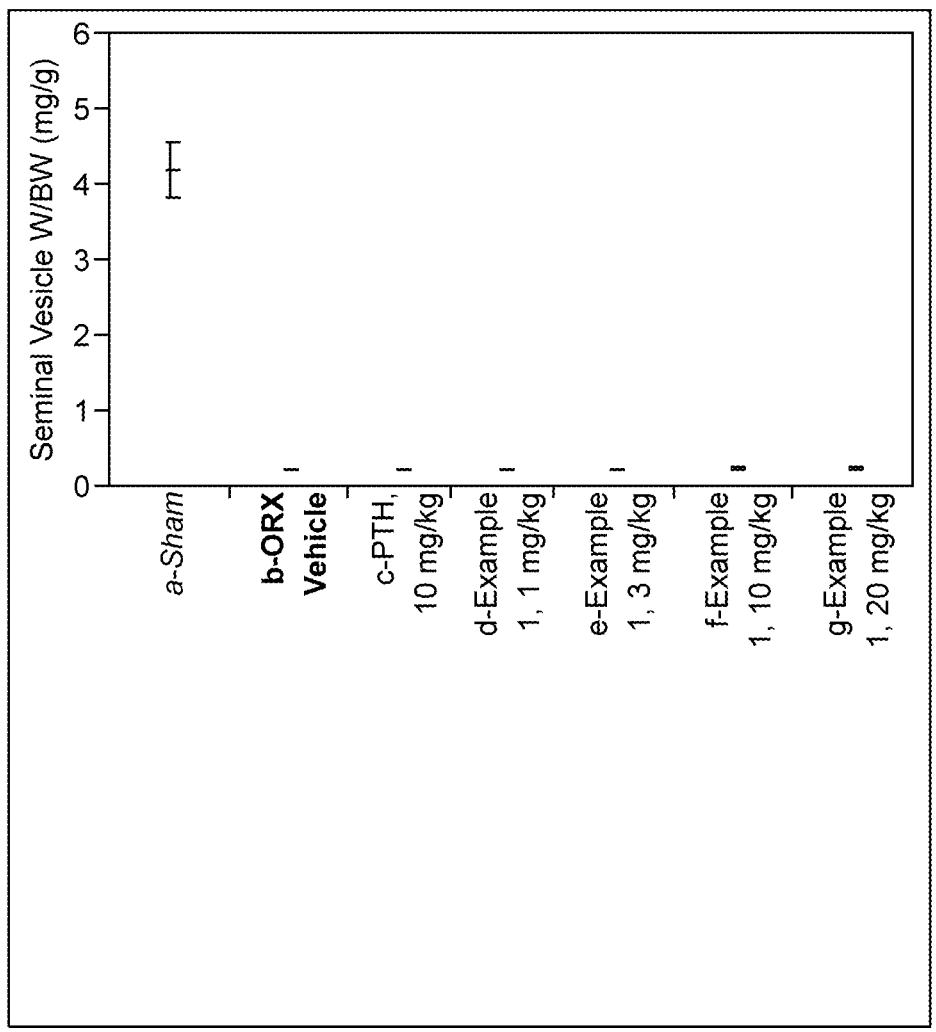
FIG. 1 illustrates that Example 1 resulted in no significant accrual of seminal vesicle weight after treatment of 8 weeks in a rat orchidectomized for 8 weeks and which was hyper responsive to any androgenic stimulation.

The AR modulator compound (S)-(7-cyano-4-pyridin-2-ylmethyl-1,2,3,4-tetrahydro-cyclopenta[b]indol-2-yl)-carbamic acid isopropyl ester, alternatively represented as carbamic acid, N-[(2S)-7-cyano-1,2,3,4-tetrahydro-4-(2-pyridinylmethyl)cyclopent[b]indol-2-yl]-, 1-methylethyl ester, represented by the structural formula I, has been shown to increase lean muscle mass and decrease fat mass in healthy volunteers. Further, no significant changes in hematocrit or change in prostate specific antigen (PSA) was observed after treatment with (S)-(7-cyano-4-pyridin-2-ylmethyl-1,2,3,4-tetrahydro-cyclopenta[b]indol-2-yl)-carbamic acid isopropyl ester after 12 weeks in healthy volunteers. Furthermore, treatment of orchidectomized rats with (S)-(7-cyano-4-pyridin-2-ylmethyl-1,2,3,4-tetrahydro-cyclopenta[b]indol-2-yl)-carbamic acid isopropyl ester shows no significant accrual of seminal vesicle weight.

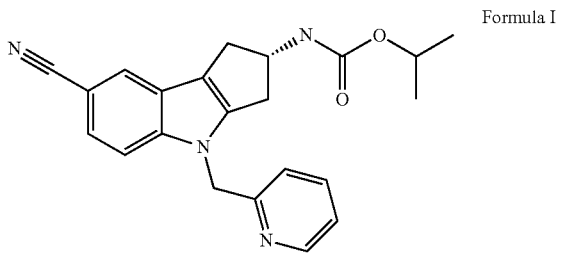 [SMILES: CC(C)OC(=O)N[C@H]1Cc2c(n(Cc3ccccn3)c3ccc(C#N)cc23)C1]

Formula I

Accordingly, the present invention provides a method of treating the symptoms as a result of secondary hypogonadism induced by ADT, comprising administering to a patient in need of such treatment an effective amount the compound of Formula I. In a further embodiment, the patient is a prostate cancer patient. In a further embodiment, the present invention provides a method of treating the loss in bone mass, bone strength, muscle mass, or muscle strength as a result of secondary hypogonadism induced by ADT. In another further embodiment, the present invention provides a method of treating loss of libido and hot flashes as a result of secondary hypogonadism induced by ADT.

Further, the present invention provides the use of a compound of Formula I, or a pharmaceutically acceptable salt thereof, in therapy, in particular for treating the symptoms of ADT for patients in need thereof. In a further embodiment, the patient is a prostate cancer patient. Further, the present invention provide the use of a compound of Formula I, or a pharmaceutically acceptable salt thereof, in treating the symptoms as a result of secondary hypogonadism induced by ADT. Even further, the present invention provides the use of a compound of Formula I, or a pharmaceutically acceptable salt thereof, in treating the symptoms of ADT for prostate cancer patients. In a further embodiment, the present invention provides the use of a compound of the invention, or a pharmaceutically acceptable salt thereof, for the manufacture of a medicament for treating the symptoms of ADT for prostate cancer patients. In a further embodiment, the present invention provides the use of a compound of the invention, or a pharmaceutically acceptable salt thereof, for the manufacture of a medicament for treating the symptoms as a result of secondary hypogonadism induced by ADT.

Further, the present invention provides the use of a compound of Formula I, or a pharmaceutically acceptable salt thereof, in therapy, in particular for treating the loss in bone mass, bone strength, muscle mass, or muscle strength as a result of secondary hypogonadism induced by ADT. Even further, the present invention provides the use of a compound of Formula I, or a pharmaceutically acceptable salt thereof, in treating the loss in bone mass, bone strength, muscle mass, or muscle strength as a result of secondary hypogonadism induced by ADT. In a further embodiment, the present invention provides the use of a compound of the invention, or a pharmaceutically acceptable salt thereof, for the manufacture of a medicament for treating the loss in bone mass, bone strength, muscle mass, or muscle strength as a result of secondary hypogonadism induced by ADT.

Further, the present invention provides the use of a compound of Formula I, or a pharmaceutically acceptable salt thereof, in therapy, in particular for treating loss of libido and hot flashes as a result of secondary hypogonadism induced by ADT. Even further, the present invention provides the use of a compound of the invention, or a pharmaceutically acceptable salt thereof, in treating loss of libido and hot flashes as a result of secondary hypogonadism induced by ADT. In a further embodiment, the present invention provides the use of a compound of the invention, or a pharmaceutically acceptable salt thereof, for the manufacture of a medicament for treating loss of libido and hot flashes as a result of secondary hypogonadism induced by ADT.

An androgen receptor modulator compound of Formula I, and methods of making and using said compounds as useful therapeutic agents for therapeutic indications such as hypogonadism, reduced bone mass or density, and reduced muscle mass or strength, are recited in US-2010-0069404, published Mar. 18, 2010, incorporated herein by reference. See also WO 2008/063867. An androgen receptor (AR) modulator compound of Formula I is a potent and selective modulator of the androgen receptor.

More specifically, the present invention provides a method of treating the symptoms of ADT for prostate cancer patients, comprising administering to a patient in need of such treatment an effective amount of a compound of Formula I, represented structurally as:

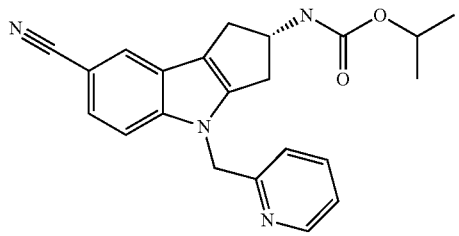 [SMILES: CC(C)OC(=O)N[C@H]1Cc2c(n(Cc3ccccn3)c3ccc(C#N)cc23)C1]

or a pharmaceutically acceptable salt thereof.

As used herein, the term "patient" refers to a human.

As used herein, the terms "treating", "to treat", or "treatment", include restraining, slowing, stopping, reducing, or reversing the progression or severity of an existing symptom, disorder, condition, or disease.

As used herein, the terms "T1-T4" refer to the T category of the TNM staging system of the American Joint Committee on Cancer (AJCC) to describe how far a cancer has spread. The T category indicates the presence of tumors and describes the extent of the primary tumor. Higher numbers indicate increased size, extent, or degree of penetration. Each cancer type has specifics to classify under the number. For prostate cancer, T1 indicates that the doctor cannot feel the tumor or see it with imaging such as transrectal ultrasound. T2 indicates that the doctor can feel the cancer with a digital rectal exam (DRE) or see it with imaging such as transrectal ultrasound, but it still appears to be confined to the prostate gland. T3 indicates that the cancer has begun to grow and spread outside the prostate and may have spread into the seminal vesicles. T4 indicates that the cancer has grown into tissues next to the prostate (other than the seminal vesicles), such as the urethral sphincter (muscle that helps control urination), the rectum, the bladder, and/or the wall of the pelvis.

As used herein, the term "effective amount" refers to the amount or dose of compound of Formula I, or a pharmaceutically acceptable salt thereof, upon administration to the patient, provides the desired effect in the patient under diagnosis or treatment. In determining the effective amount for a patient, a number of factors are considered by the attending diagnostician, including, but not limited to the patient's size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of Formula I and its pharmaceutically acceptable salts are generally effective over a broad dosage range. For example, dosages per day of individual agents normally fall within the range of about 1 mg/day to about 1000 mg/day, preferably about 1 mg/day to about 500 mg/day, about 1 mg/day to about 250 mg/day, about 1 mg/day to about 100 mg/day, 1 mg/day to about 75 mg/day, and 1 mg/day to about 25 mg/day. Most preferably, dosages per day of individual agents normally fall within the range of about 1 mg/day to about 5 mg/day. Most preferably the compound of Formula I is used at a dose per day selected from 1 mg, 5 mg, 25 mg, and 75 mg per day.

An androgen receptor modulator compound of Formula I is preferably formulated as a pharmaceutical composition administered by any route which makes the compound bioavailable. The route of administration may be varied in any way, limited by the physical properties of the drugs and the convenience of the patient and the caregiver. Preferably, an androgen receptor modulator compound of Formula I is formulated for oral or parenteral administration including intravenous or subcutaneous administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

It is preferred that the compound of Formula I is the free base.

Preparations and Example

The following methods, preparations and examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art. The specific synthetic steps for each of the routes described may be combined in different ways, or in conjunction with steps from different procedures, to prepare a compound of Formula I, or salts thereof. The products of each step can be recovered by conventional methods well known in the art, including extraction, evaporation, precipitation, chromatography, filtration, trituration, and crystallization. In addition, all substituents unless otherwise indicated, are as previously defined.

Unless noted to the contrary, the compounds illustrated herein can be named and numbered using Accelrys® Draw version 4.0 (Accelrys, Inc., San Diego, Calif.), IUPACNAME ACDLABS, or ChemDraw® Ultra 12.0. The R or S configuration of the compound of the invention may be determined by standard techniques such as X-ray analysis and correlation with chiral-HPLC retention time. Individual isomers, enantiomers, and diastereomers may be separated or resolved by one of ordinary skill in the art at any convenient point in the synthesis of compound of Formula I by methods such as selective crystallization techniques or chiral chromatography (See for example, J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994). Designations "isomer 1" and "isomer 2" refer to the compounds that elute from chiral chromatography first and second, respectively, and if chiral chromatography is initiated early in the synthesis, the same designation is applied to subsequent intermediates and examples. Additionally, certain intermediates described in the following schemes may contain one or more nitrogen protecting groups. The variable protecting group may be the same or different in each occurrence depending on the particular reaction conditions and the particular transformations to be performed. The protection and de-protection conditions are well known to the skilled artisan and are described in the literature (See for example "Greene's Protective Groups in Organic Synthesis", Fourth Edition, by Peter G. M. Wuts and Theodora W. Greene, John Wiley and Sons, Inc. 2007).

The reagents and starting materials are readily available to one of ordinary skill in the art. U.S. Pat. No. 7,968,587, incorporated herein by reference, discloses the synthesis of (S)-(7-cyano-4-pyridin-2-ylmethyl-1,2,3,4-tetrahydro-cyclopenta[b]indol-2-yl)-carbamic acid isopropyl ester.

As used herein, the following terms have the meanings indicated: "ADME" refers to absorption, distribution, metabolism and excretion; "DMAC" refers to N,N-dimethylacetamide; "DMF" refers to dimethylformamide; "ECG" refers to electrocardiographic; "EDTA" refers to ethylenediaminetetraacetic acid; "ee" refers to enantiomeric excess; "EtOAc" refers to ethyl acetate; "EtOH" refers to ethanol; "HOAc" refers to acetic acid; "HPLC" refers to high performance liquid chromatography; "LCMS" refers to liquid chromatography mass spectrometry; "LY" refers to Example 1; "MeOH" refers to methanol; "min" refers to minutes; "MS" refers to mass spectrometry; "MTBE" refers to tert-butylmethyl ether; "NOAEL" refers to no observable adverse effect level; "Orx" refers to orchidectomized; "SE" refers to standard error; "TE" refers to testosterone enanthate; "TFA" refers to trifluoroacetic acid; "THF" refers to tetrahydrofuran; and "UV" refers to ultraviolet.

Intermediate 1

(±)-2-(1,3-Dioxo-1,3-dihydro-isoindol-2-yl)-1,2,3,4-tetrahydro-cyclopenta[b]indole-7-carbonitrile Mix (±)-2-(3-oxo-cyclopentyl)-isoindole-1,3-dione (12.7 g, 55.3 mmol) and 4-cyanophenylhydrazine-HCl (8.53 g, 50.3 mmol) in HOAc (200 mL) and 4N HCl dioxane (50 mL). Using mechanical stirring, heat the reaction to 90° C. for 18 h, then add additional 4N HCl dioxane (20 mL). Heat the reaction to 100° C. for 18 h. Dilute the reaction mixture with water (600 mL) and collect a black solid by vacuum filtration. Sonicate the solid with MeOH (200 mL), then collect and dry in a vacuum oven to give 10.94 g (66%) of a gray-brown solid. MS (m/z): 328 (M+H), 326 (M−H).

Intermediate 2

(±)-2-(1,3-Dioxo-1,3-dihydro-isoindol-2-yl)-4-pyridin-2-ylmethyl-1,2,3,4-tetrahydro-cyclopenta[b]indole-7-carbonitrile

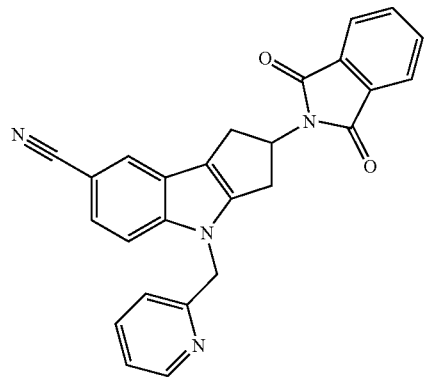 [SMILES: N#Cc1ccc2c(c1)c1c(n2Cc2ccccn2)CC(N2C(=O)c3ccccc3C2=O)C1]

Heat a mixture of 2-(1,3-dioxo-1,3-dihydro-isoindol-2-yl)-1,2,3,4-tetrahydro-cyclopenta[b]indole-7-carbonitrile (5 g, 15.3 mmol) in DMF (25 ml) to 40° C. Add cesium carbonate (10.4 g, 32.4 mmol) and 2-bromomethylpyridine hydrobromide (4.05 g, 16 mmol). Stir the mixture at 40° C. for 24 h. Add the mixture to water (250 mL) and stir for 1 h. Filter the solids and dry the collected material under vacuum. Add the solid to EtOH (25 mL) and reflux for 30 min. Cool the mixture to 22° C. and filter. Dry the solid under vacuum to constant weight to provide 4.8 g (75%) of the title compound. MS (m/z): 419 (M+H).

Intermediate 3

(±)-2-Amino-4-pyridin-2-ylmethyl-1,2,3,4-tetrahydro-cyclopenta[b]indole-7-carbonitrile Hydrochloride

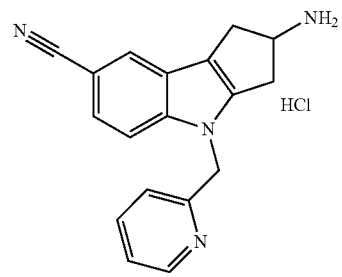 [SMILES: N#Cc1ccc2c(c1)c1c(n2Cc2ccccn2)CC(N)C1 ; Cl]

Add 2-(1,3-dioxo-1,3-dihydro-isoindol-2-yl)-4-pyridin-2-ylmethyl-1,2,3,4-tetrahydro-cyclopenta[b]indole-7-carbonitrile (77 g, 184 mmol) to THF (1.3 L) and EtOH (230 mL). Stir the mixture for 10 min and then add hydrazine monohydrate (20 mL, 400 mmol). Stir the mixture at 22° C. for 16 h. Filter the mixture and evaporate the mother liquors. Dissolve the residue in dichloromethane (300 mL). Add a solution of 4M HCl in dioxane (50 mL) and stir the mixture for 2 h. Filter and dry the isolated solid under vacuum to constant weight to provide 54 g (90%) of the title compound. MS (m/z): 289 (M+H).

EXAMPLES

Example 1

(S)-(7-Cyano-4-pyridin-2-ylmethyl-1,2,3,4-tetrahydro-cyclopenta[b]indol-2-yl)-carbamic Acid Isopropyl Ester

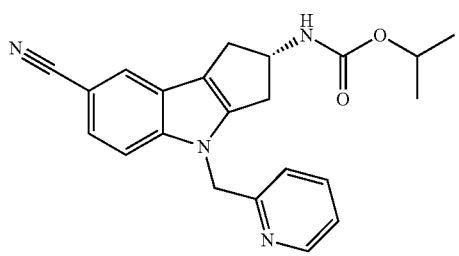 [SMILES: CC(C)OC(=O)N[C@H]1Cc2c(n(Cc3ccccn3)c3ccc(C#N)cc23)C1]

Step 1: (±)-(7-Cyano-4-pyridin-2-ylmethyl-1,2,3,4-tetrahydro-cyclopenta[b]indol-2-yl)-carbamic Acid Isopropyl Ester

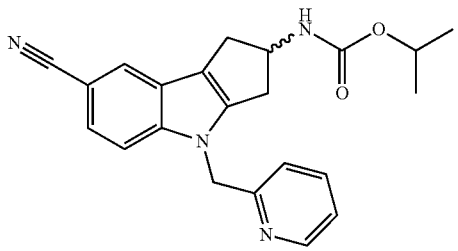 [SMILES: CC(C)OC(=O)NC1Cc2c(n(Cc3ccccn3)c3ccc(C#N)cc23)C1]

To a solution of (±)-2-amino-4-pyridin-2-ylmethyl-1,2,3,4-tetrahydro-cyclopenta[b]indole-7-carbonitrile (2.32 g, 8.05 mmol) and diisopropylethylamine (9.65 mmol, 1.68 mL) in dichloromethane (10 mL), add isopropylchloroformate (8.86 mmol, 8.9 mL) and stir at room temperature overnight. Dilute with ethyl acetate and wash with 10% $K_2CO_3$ solution (2×). Dry the organic portion over $Na_2SO_4$, filter, and concentrate to obtain 3.3 g. Purify by column chromatography (0-100% ethyl acetate/dichloromethane) to obtain 2.48 g (82%) of the racemic product. LCMS 375.2 (M+H).

Alternate Procedure:

Add (±)2-amino-4-pyridin-2-ylmethyl-1,2,3,4-tetrahydro-cyclopenta[b]indole-7-carbonitrile hydrochloride (35 g, 108 mmol) to a mixture of dichloromethane (350 mL) and pyridine (70 mL). Stir the mixture under nitrogen and cool to 5° C. Add isopropyl chloroformate (1M solution in toluene, 162 mL, 162 mmol). Remove the ice bath and stir the mixture at 22° C. After 16 h evaporate the solvent. Add the resulting residue to water (350 mL) and stir 2 h. Filter and dry the collected solid under vacuum at 45° C. Add the solid to ethyl acetate (400 mL) and heat the mixture to reflux. Then cool to 22° C. and filter the solid. Add the wet solid to ethyl acetate (200 mL) and heat to reflux for 30 min. Cool the mixture to 22° C. during one hour and then cool to 0-5° C. during 5 min. Filter the mixture and dry the isolated solid under vacuum to constant weight to provide 23 g (62%) of the title compound. MS (m/z): 374 (M+H).

Step 2: (R)- and (S)-(7-Cyano-4-pyridin-2-ylmethyl-1,2,3,4-tetrahydro-cyclopenta[b]indol-2-yl)-carbamic Acid Isopropyl Ester Separate enantiomers of Example 1 by preparative chiral chromatography using Chiralpak AD column (8×33 cm), eluting with 100% EtOH at 375 mL/min and 250 nm. Isomer 1 (R): 1.14 g, 99.9% ee (analytical conditions: Chiralpak AD-H column, eluting with 100% EtOH/0.2% dimethylethylamine; LCMS 375.2 (M+H). Isomer 2 (S): 1.67 g, 99.4% ee; LCMS 375.2 (M+H).

Alternate Route to Example 1, Isomer 2: (S)-(7-Cyano-4-pyridin-2-ylmethyl-1,2,3,4-tetrahydro-cyclopenta[b]indol-2-yl)-carbamic Acid Isopropyl Ester Add (S)-7-cyano-1,2,3,4-tetrahydro-cyclopenta[b]indol-2-yl)-carbamic acid isopropyl ester (13 g, 41.3 mmol) to DMF (100 mL) and warm the solution to 40° C. Add cesium carbonate (42 g, 129 mmol) in one portion and stir the mixture for 30 min at 40° C. Add 2-bromomethylpyridine hydrobromide 21 g, 83 mmol) portionwise over 4 h. Stir the mixture at 40° C. for 18 h. Add the mixture to chilled water (1 L) at 0 to 5° C. and stir for 30 min Isolate the solid by filtration and dry under vacuum to constant weight. Pass the material over a silica gel pad eluting with $CH_2Cl_2$/EtOAc (7/3). Combine the fractions containing the product and evaporate the solvent to give a pale brown solid. Rrecrystallize from ethyl acetate to give 15.3 g (77%) of the title compounds. LC/MS (m/z) 375 (M+H).

Second Alternate Route:

(HPLC conditions—column: Zorbax® SB-Phenyl, Rapid Resolution, 4.6×75 mm, 3.5 micron; solvent: 10% acetonitrile/90% water with 0.05% TFA; UV at 230 nm)

Step 1: (±)-(7-Cyano-1,2,3,4-tetrahydro-cyclopenta[b]indol-2-yl)-carbamic Acid tert-butyl Ester Equip a 12 L 3-necked round bottom flask with overhead agitation, thermocouple, addition funnel, nitrogen inlet, and cooling bath. Charge the flask with (±)-2-(1,3-dioxo-1,3-dihydro-isoindol-2-yl)-1,2,3,4-tetrahydro-cyclopenta[b]indole-7-carbonitrile (500 g, 1.53 moles) and THF (5 L). Stir the resulting slurry at ambient temperature. Add hydrazine monohydrate (185.6 mL, 3.82 moles) in a slow stream from an addition funnel over 10 minutes. Stir the resulting mixture at ambient temperature overnight (about 18 h). Add cool water to the bath and charge the addition funnel with di-t-butyl dicarbonate (875.1 g, 4.01 moles; previously melted to a liquid). Add to the reaction mixture over 2 hours, keeping the pot temperature below 30° C. After 15 min, analyze by HPLC to find complete consumption of the intermediate amine Filter the reaction mixture onto a polypropylene pad in a stainless steel, table-top filter, and wash the resulting filter cake with ethyl acetate (2×1 L). Concentrate the filtrate in vacuo to remove most of the THF. Purify the resulting mixture (about 1 L) over a plug of silica gel (4 Kg Kieselgel-60), eluting with ethyl acetate. Concentrate the recovered eluent in vacuo to a dark oil. Add heptane (2 L) and ethyl acetate (350 mL) and spin the contents on a rotary evaporator at ambient temperature for 2 h. Add ice to the bath and spin the resulting slurry at 5° C. for an additional 2 h. Filter the solids, rinse with 90/10 heptane/ethyl acetate (2×500 mL) and vacuum dry at 35° C. Obtain the titled compound as a light tan solid in 91.6% yield.

Step 2: (±)-(7-Cyano-4-pyridin-2-ylmethyl-1,2,3,4-tetrahydro-cyclopenta[b]indol-2-yl)-carbamic Acid Tert-Butyl Ester Equip a 20 L bottom outlet flask with overhead agitation, thermocouple, and nitrogen inlet. Charge the flask with (±)-(7-cyano-1,2,3,4-tetrahydro-cyclopenta[b]indol-2-yl)-carbamic acid tert-butyl ester (500 g, 1.68 moles) and dichloromethane (5 L). Begin agitation and add tetra n-butylammonium hydrogen sulfate (58.9 g, 0.168 mol) followed by 2-(bromomethyl)pyridine hydrobromide (510.4 g, 2.02 moles). Add deionized water (2 L) followed by a 50% NaOH solution (445.3 mL, 8.41 moles). Stir the resulting mixture vigorously overnight (about 21 h). Stop the agitation, allow the layers to separate, and discard the aqueous (upper) layer. Wash the organics with deionized water (3×4 L), dry over sodium sulfate, and concentrate in vacuo to about 500 mL. Purify the crude material over a silica gel plug (7 Kg Keiselgel 60) using 1:1 ethyl acetate/heptane as eluent.

Concentrate the eluent in vacuo to afford 560 grams of the titled compound as an off-white solid (81.4%).

Step 3: Isomer 1, (R)- and Isomer 2, (S)-(7-Cyano-4-pyridin-2-ylmethyl-1,2,3,4-tetrahydro-cyclopenta[b]indol-2-yl)-carbamic Acid Tert-Butyl Ester Use the following analytical chiral HPLC method to analyze enantiomers: 4.6×150 mm Chiralpak AD-H column (Chiral Technologies), 20:80:0.2 acetonitrile/3A grade denatured ethanol/dimethylethylamine mobile phase, 0.6 mL/min flow rate, UV detection @ 255 nm. Enantiomer 1 elutes at 4.0 min and enantiomer 2 elutes at 5.2 min. An 8% impurity (255 nm) elutes at 3.6 min Purify (±)-(7-cyano-4-pyridin-2-ylmethyl-1,2,3,4-tetrahydro-cyclopenta[b]indol-2-yl)-carbamic acid tert-butyl ester (528 g) by preparative chiral HPLC using the following conditions: 8×33 cm Chiralpak AD column, same mobile phase as analytical, 375 mL/min flow rate, UV detection at 270 nm. Dissolve 108 g of sample in the mobile phase at a final concentration of 75 mg/mL final. Load 4.0 g/injection with the enantiomer 1 fraction eluting between 3.5-5.5 min. and enantiomer 2 eluting between 6-10 min. Set the final run time at 7.5 min/injection with partial stacking of the enantiomer 2 profile eluting just after each injection to reduce solvent consumption. Purify the remaining 420 g over a plug of silica using Merck 9385 60 Angstrom 230-400 mesh silica gel, eluting with a 1:2:7 dichloromethane/heptane/methyl t-butyl ether solvent system. Use a 3.5 kg silica pad with vacuum filtration at 140 g sample/plug. Racemate begins to emerge after 5 column volumes. Use 100% methyl t-butyl ether followed by 100% acetone to push the remaining racemate off the plug. Obtain a total of 358.5 g of 98+% pure racemate in this manner Resolve this material as above by preparative chiral HPLC. Obtain 208.8 g (99.9% ee) of enantiomer 1 (R isomer) and 197 g (99.6% ee) of enantiomer 2 (S isomer).

Step 4: (S)-2-Amino-4-pyridin-2-ylmethyl-1,2,3,4-tetrahydro-cyclopenta[b]indole-7-carbonitrile Hydrochloride Equip a 3 L 3-necked round bottom flask with a heating mantle, air stirrer, temperature probe, nitrogen inlet, and addition funnel. Charge the flask with (S)-(7-cyano-4-pyridin-2-ylmethyl-1,2,3,4-tetrahydro-cyclopenta[b]indol-2-yl)-carbamic acid tert-butyl ester (85.0 g, 0.22 moles), and EtOH (850 mL). Add concentrated HCl (180 mL, 2.20 moles) in one portion. Heat the resulting solution to 45-50° C. and stir for 90 min, after which analyze by HPLC to indicate complete consumption of starting material. Transfer the mixture to a Buchi flask, dilute with deionized water (595 mL), and concentrate in vacuo to remove EtOH. Add EtOAc in two portions (2×170 mL) and re-strip to remove both the EtOAc and residual EtOH. Transfer the aqueous concentrate to a 5 L reaction flask, and cool to 10-15° C. While maintaining the temperature of the reaction at <30° C., adjust the pH of the solution to 11-12 by the drop-wise addition of 5 M NaOH (950 mL). Extract the resulting mixture with $CH_2Cl_2$ (1300 mL, 800 mL). Wash the combined $CH_2Cl_2$ extracts with deionized water (500 mL), dry over $Na_2SO_4$, and concentrate in vacuo to afford titled compound as a light green solid (65.0 g, 103%).

Step 5: (S)-(7-Cyano-4-pyridin-2-ylmethyl-1,2,3,4-tetrahydro-cyclopenta[b]indol-2-yl)-carbamic Acid Isopropyl Ester

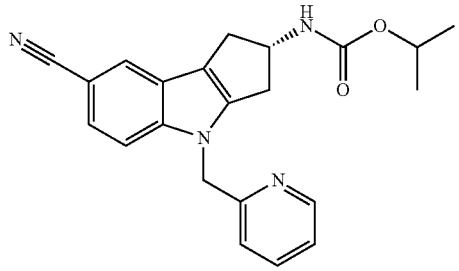 [SMILES: CC(C)OC(=O)N[C@H]1Cc2c(n(Cc3ccccn3)c3ccc(C#N)cc23)C1]

Equip a 2 L reaction flask with a cooling bath, air stirrer, temperature probe, and addition funnel. Charge the flask with (S)-2-amino-4-pyridin-2-ylmethyl-1,2,3,4-tetrahydro-cyclopenta[b]indole-7-carbonitrile hydrochloride (62.8 g, 0.218 moles), DMF (188 mL), and triethylamine (33.4 mL, 0.240 mol). Cool the resulting solution to 0° C. using an ice/acetone bath. While maintaining the temp at <10° C., add isopropyl chloroformate (218 mL, 0.218 mol, 1 M in toluene) drop-wise via an addition funnel. When the addition is complete, remove the cooling bath and allow the mixture to warm to ambient temperature. After 1 hour, analyze by HPLC to indicate the reaction is complete, and pour the mixture into a solution of deionized water (1256 mL) and EtOAc (1884 mL). Separate the layers, filter the organic layer, and re-wash with a 1:1 water:brine solution, then dry over $Na_2SO_4$. Concentrate in vacuo at 55° C. to about 15 volumes, and allow the resulting to cool to ambient temperature, affording a white precipitate. Add heptane (628 mL) and stir for 20 min. Concentrate the mixture back to about 15 volumes. Filter the solids, wash with heptane, and dry to give the titled compound as a fluffy white solid (68.9 g, 84.5%). $^1$H NMR (500 MHz, DMSO-$d_6$), δ 8.49 (dd, 1H), 7.86 (d, 1H, J=1.5), 7.71-7.75 (m, 1H), 7.60 (d, 1H, J=9.0), 7.57 (d, 1H, J=9.0), 7.36 (dd, 1H), 7.28-7.26 (m, 1H), 7.14 (d, 1H, J=7.5), 5.44 (s, 2H), 4.79-4.72 (m, 1H), 4.71-4.66 (m, 1H), 3.22-3.20 (m, 1H), 3.16-3.12 (m, 1H), 2.73-2.66 (m, 2H), 1.16 (dd, 6H).

$3^{rd}$ Alternate Synthesis

Step 1

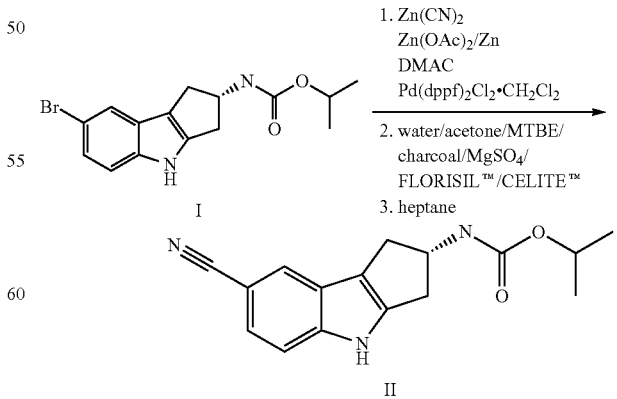

Treat (7-Bromo-1,2,3,4-tetrahydro-cyclopenta[b]indo-2-yl)-carbamic acid isopropyl ester (I) with $Zn(CN)_2$, Zn(OAc)$_2$, Zn, and Pd(dppf)$_2$Cl$_2$·CH$_2$Cl$_2$ in DMAC to afford the (7-cyano-1,2,3,4-tetrahydro-cyclopenta[b]indol-2-yl-carbamic acid isopropyl ester (II). Add water to precipitate technical grade II. Re-dissolve Intermediate II in a mixture of MTBE and acetone and filter the resulting slurry to remove the inorganic components. Treat the filtrate containing II with charcoal, MgSO$_4$, and FLORISIL™ prior to isolation of II as a crystal solid upon heptane crystallization.

Step 2

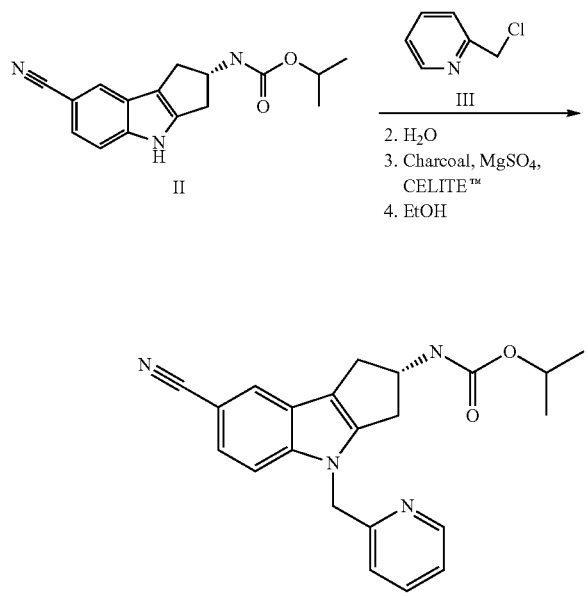

React Intermediate II with 2-picolyl chloride hydrochloride (III) and K$_2$CO$_3$ in DMAC to give technical grade Example 1. Isolate technical grade Example 1 by addition of water and filtration. Recrystallize three times from EtOH to afford Example 1.

Assays, In Vivo Studies, and Clinical Studies

Orchidectomized Rat Assay

A total of 86 virgin male Sprague-Dawley rats (Harlan Sprague Dawley Inc) are used. 14 rats are sham-operated and 72 rats are castrated at 6 months of age. The rats are maintained on a 12 hr light/dark cycle at 22° C. with ad lib access to food (TD 89222 with 0.5% Ca and 0.4% P, Teklad, Madison, Wis.) and water. Orx rats are allowed to lose bone for 2 months, weighed and randomized into treatment groups, as detailed in Table 1 below. Groups 1 and 2 are sacrificed on the first day as the baseline controls, groups 3 and 4 Sham and Orx controls are be administered vehicle (0.25% CMC/Twin80). Group 5 is given PTH (1-38) sc as an injection. Groups 6-13 are administered SARMs orally via gavage. All the treatments are once daily for 2 months.

TABLE 1

| Group No | Treatment Group | 8 month Day 0 | 10 month Day 60 | Delivery Route |
|---|---|---|---|---|
| 1 | Sham | | 7 | po |
| 2 | Orx | | 6 | po |
| 3 | Pre-Sham | | 7 | po |
| 4 | Pre-Orx | | 7 | po |
| 5 | Orx + PTH (10 ug/Kg/d) | | 6 | sc |
| 6 | Orx + Example 1 (1 mg/Kg/d) | | 6 | po |
| 7 | Orx + Example 1 (3 mg/Kg/d) | | 7 | po |
| 8 | Orx + Example 1 (10 mg/Kg/d) | | 7 | po |
| 9 | Orx + Example 1 (20 mg/Kg/d) | | 7 | po |

For dynamic histomorphometry, all rats except for base lines receive xylenol orange 90 mg/kg sc at the first day the treatment initiated. All the rats are given calcein 10 mg/kg s.c on days 14, 13 and on days 4, 3 before sacrifice.

Sample Preparations:

PTH (1-38) (Zeneca (Cambridge Research Biochemicals) Ref #-DG-12-14071, Batch 14071): acidified saline vehicle with 2% inactivated rat serum EXAMPLE 1: 1% CMC/0.25% Tween 80 0.5 ml/rat based on body wt.

Endpoints & Parameters Measured

1. Body weight: before and bi weekly, dosing volume adjusted accordingly

2. NMR: beginning and at end of the study

3. Muscle: wet weights are obtained from the left gastrocnemius, quadriceps, soleus, levator ani, Seminal Vesicle (SV), prostate, and heart, then collected for RNA or histology analysis.

4. Terminal serum samples are collected from all animals and stored at −80° C. in 1×100 µl (OCN), 2×150 (IGF-1 and store), 1×300 µl (Chem 18), 2×500 µl (one for BSALP, and store).

5. Bone Collection: One femur and lumbar vertebrae are fixed (in 50/50 ethanol/saline) for CT and biomechanical test; One tibia is collected for PALP/calcein analysis with epiphysis tear off (in 70% ethanol), another tibia is collected for histomorphometric analyses (70% ethanol).

4. PK determination: A few days before taking down, 3 rats in each dose group (n=3 of test articles only) are subject to tail bleeding to get approximately 0.2 ml of blood in EDTA tubes at the following time points: 0.25, 0.5, 1, 2, 3, 4, 8 and 24 hours. Samples are transferred to ADME for plasma concentration analysis.

TABLE 2

| Group No | Treatment Group | SV Weight, % Sham |
|---|---|---|
| 2 | Orx | 5.7 |
| 5 | Orx + PTH (10 ug/Kg/d) | 5.6 |
| 6 | Orx + Example 1 (1 mg/Kg/d) | 5.6 |
| 7 | Orx + Example 1 (3 mg/Kg/d) | 5.5 |
| 8 | Orx + Example 1 (10 mg/Kg/d) | 6.0 |
| 9 | Orx + Example 1 (20 mg/Kg/d) | 6.1 |

Following a protocol essentially as described above, Example 1 resulted in no significant accrual of seminal vesicle weight after treatment of 8 weeks in a rat orchidectomized for 8 weeks and which was hyper responsive to any androgenic stimulation.

TABLE 3

| Group No | Treatment Group | LV-TBMC (mg) ± SD | LV-TBMD (mg/cm3) ± SD | LV-TA (cm2) ± SD |
|---|---|---|---|---|
| 1 | Sham | 1.7871 ± 0.0509 | 574.471 ± 13.385 | 0.3463 ± 9.71E−03 |
| 2 | Orx | 1.5814 ± 0.0521 | 508.314 ± 13.037 | 0.3456 ± 7.61E−03 |
| 3 | Orx + Example 1 (1 mg/Kg/d) | 1.54 ± 0.0256 | 507.4 ± 6.931 | 0.3378 ± 7.08E−03 |
| 4 | Orx + Example 1 (3 mg/Kg/d) | 1.79 ± 0.095 | 549 ± 15.965 | 0.362 ± 0.0138 |
| 5 | Orx + Example 1 (10 mg/Kg/d) | 1.7757 ± 0.0607 | 562.843 ± 16.104 | 0.3521 ± 0.0125 |
| 6 | Orx + Example 1 (20 mg/Kg/d) | 1.6943 ± 0.0264 | 529.357 ± 10.052 | 0.3563 ± 0.0102 |

Figure 2:
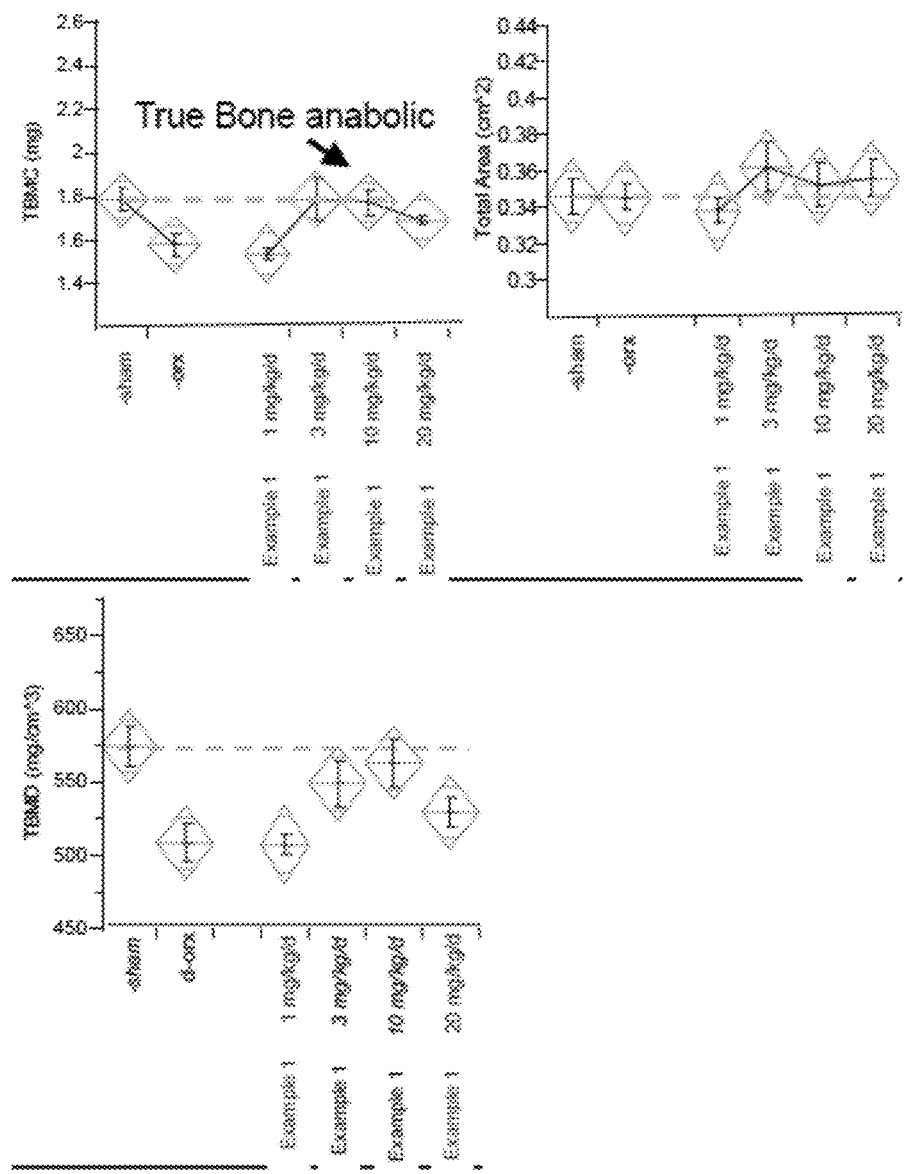
FIG. 2 illustrates that Example 1 resulted in significant accrual of, lumbar vertebra trabecular bone mineral density (LV-TBMD) and showed a trend towards increase in lumbar vertebra trabecular bone mineral content (LV-TBMC), and cross-sectional area (LV-TA) after treatment of 8 weeks in a rat orchidectomized for 8 weeks.

Treatment with Example 1 resulted in significant accrual of, lumbar vertebra trabecular bone mineral density (LV-TBMD) and showed a trend towards increase in lumbar vertebra trabecular bone mineral content (LV-TBMC), and cross-sectional area (LV-TA) after treatment of 8 weeks in a rat orchidectomized for 8 weeks as shown in FIG. 2 and Table 3.

In Vivo Study to Explore Direct Antagonist Effect of Example 1 in the Presence of TE A total of 36 ORX and 6 sham-operated Wistar male rats are used (orchidectomized at 8 weeks of age and allowed to waste for 4 weeks). The rats are maintained on a 12 hr light/dark cycle at 22° C. with ad lib access to food (TD 5001 with 0.95% Ca and 0.67% P, Teklad, Madison, Wis.) and water. Rats are randomized and placed into treatment groups (n=6) based on body weight. Route of administration for all groups except TE is oral. TE is administered subcutaneously. At the end of 8 weeks of daily dosing, rats are euthanized, weighed & tissue harvested. Levator ani, prostates, and seminal vesicles are collected from each animal. Results are plotted as means±SE.

TABLE 4

| Group No | Treatment Group | 3 month Day 0 | 5 month Day 60 | Delivery Route, Ex. 1 | Delivery Route, TE |
|---|---|---|---|---|---|
| 1 | Sham | | 6 | po | Sc |
| 2 | ORX + TE, 1 mg/kg/d | | 6 | po | Sc |
| 3 | ORX + TE, 1 mg/kg/d + Example 1, 3 mg/kg/d | | 6 | po | Sc |
| 4 | ORX + TE, 1 mg/kg/d + Example 1, 10 mg/kg/d | | 6 | po | Sc |
| 5 | ORX + TE, 1 mg/kg/d + Example 1, 30 mg/kg/d | | 6 | po | Sc |

Figure 3:
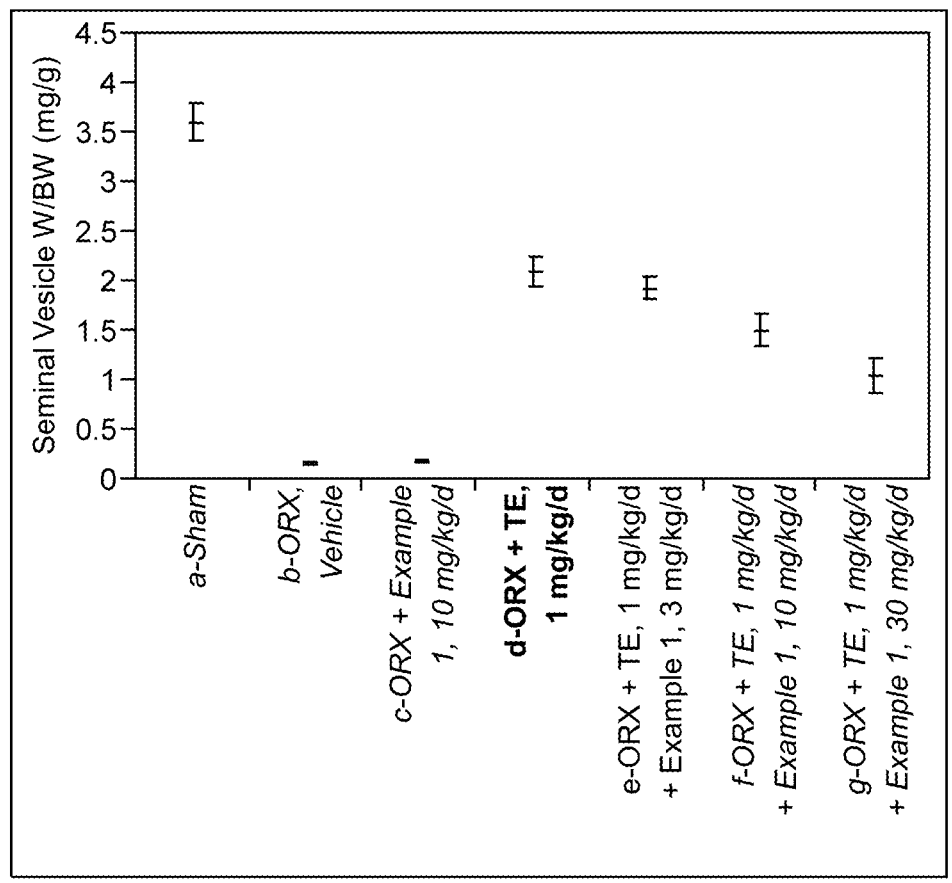
FIG. 3 illustrates that the combination with testosterone enanthate (TE) (1 mg/Kg-day) and various doses of Example 1 suggest a trend in decreasing seminal vesicle wet weight in mg normalized to body weight in grams, which is induced by TE alone.

Combination with Testosterone Enanthate (1 mg/Kg-day) and various doses of Example 1 suggest a trend in decreasing seminal vesicle wet weight in mg normalized to body weight in gms, which is induced by TE alone as shown in FIG. 3 and Table 4.

Means Comparisons of Seminal Vesicle Wet Weights Comparisons with a Control Using Dunnett's Method Control Group = d-ORX + TE, 1 mg/kg/d

| |d| | Alpha |
|---|---|
| 2.69715 | 0.05 |

TABLE 5

| Group No | Group | Abs(Dif) − LSD | p-Value |
|---|---|---|---|
| 1 | Sham | 0.979 | <.0001 |
| 2 | ORX + TE, 1 mg/kg/d | −0.52 | 1.0000 |
| 3 | ORX + TE, 1 mg/kg/d + Example 1, 3 mg/kg/d | −0.34 | 0.8628 |
| 4 | ORX + TE, 1 mg/kg/d + Example 1, 10 mg/kg/d | 0.078 | 0.0187 |
| 5 | ORX + TE, 1 mg/kg/d + Example 1, 30 mg/kg/d | 0.536 | <.0001 |
| 6 | ORX + Example 1, 10 mg/kg/d | 1.411 | <.0001 |
| 7 | ORX, Vehicle | 1.422 | <.0001 |

Positive values show pairs of means that are significantly different.

Figure 4:
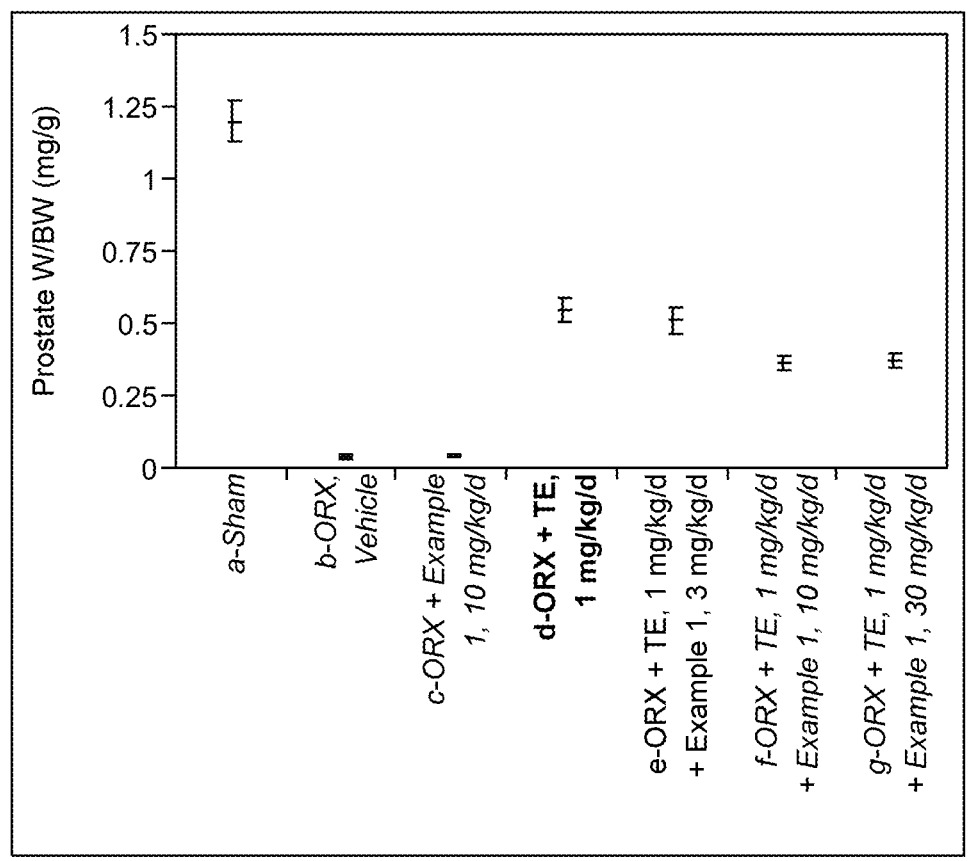
FIG. 4 illustrates that co-treatment of Example 1 to SD rats along with 1 mg/Kg TE resulted in a dose-dependent decrease in prostate wet weight in milligrams normalized to body weight in grams.

Co-treatment of Example 1 to SD rats along with 1 mg/Kg TE resulted in a dose-dependent decrease in prostate wet weight in mgs normalized to body weight in grams as shown in FIG. 4 and Table 5.

Means Comparisons of Prostate Weights Comparisons with a Control Using Dunnett's Method Control Group = d-ORX + TE, 1 mg/kg/d

| |d| | Alpha |
|---|---|
| 2.69715 | 0.05 |

TABLE 6

| Group No | Group | Abs(Dif) − LSD | p-Value |
|---|---|---|---|
| 1 | Sham | 0.509 | <.0001* |
| 2 | ORX + TE, 1 mg/kg/d | −0.15 | 1.0000 |

TABLE 6-continued

| Group No | Group | Abs(Dif) − LSD | p-Value |
|---|---|---|---|
| 3 | ORX + TE, 1 mg/kg/d + Example 1, 3 mg/kg/d | −0.11 | 0.9774 |
| 4 | ORX + TE, 1 mg/kg/d + Example 1, 30 mg/kg/d | 0.025 | 0.0167* |
| 5 | ORX + TE, 1 mg/kg/d + Example 1, 10 mg/kg/d | 0.036 | 0.0099* |
| 6 | ORX, Vehicle | 0.356 | <.0001* |
| 7 | ORX + Example 1, 10 mg/kg/d | 0.357 | <.0001* |

Positive values show pairs of means that are significantly different than TE alone group

TABLE 7

| Group No | Treatment Group | SV Weight, % Sham | Prostate Weight, % Sham |
|---|---|---|---|
| 2 | ORX + TE, 1 mg/kg/d | 58.5 | 45.5 |
| 3 | ORX + TE, 1 mg/kg/d + Example 1, 3 mg/kg/d | 53.5 | 42.7 |
| 4 | ORX + TE, 1 mg/kg/d + Example 1, 10 mg/kg/d | 42.0 | 30.3 |
| 5 | ORX + TE, 1 mg/kg/d + Example 1, 30 mg/kg/d | 29.2 | 31.2 |

TABLE 8

| | hAR Ki | LnCAP Gene Expression EC50 (nM) | | |
|---|---|---|---|---|
| | (nM) | PSA | AR | CLUSTERIN |
| R1881 | 0.38 | 0.034 | 0.035 | 0.37 |
| Example 1 | 1.95 | 2.64 | 1.64 | >100 |

Comparisons of Example 1 with the synthetic Testosterone, R1881, show that in vitro using human prostate cancer cells Example 1 is less androgenic than R1881. In contrast the biochemical binding affinity to the human Androgen receptor (Ki in nM) is only modestly reduced.

Four Week Oral Toxicity Study in Rats

This study is conducted to evaluate the potential toxicity and toxicokinetics of Example 1 in rats after 4 weeks of exposure. Three treatment groups of 10 male and 10 female CD® [Crl:CD® (SD)] rats are administered the test article at respective dose levels of 15, 150, and 1500 mg/kg/day. One additional group of 10 animals/sex serves as the control and receives the vehicle, 5% Vitamin E TPGS, 1% hydroxyethylcellulose, 0.05% Dow Corning Antifoam 1510-US in reverse osmosis-derived purified water. The test article or vehicle is administered to all groups via oral gavage, once a day for 28 consecutive days, at a dose volume of 15 mL/kg. Additionally, three groups of 18 animals/sex/group serves as toxicokinetic (TK) animals and receives the test article in the same manner and dose volume as the main study groups at respective dose levels of 15, 150, and 1500 mg/kg/day. One additional group of three animals/sex serves as the toxicokinetic control and receives the vehicle in the same manner and dose volume as the treated groups.

Observations for morbidity, mortality, injury, and the availability of food and water are conducted twice daily for all animals. Observations for clinical signs are conducted weekly for main study animals only. Body weights were measured and recorded weekly for all animals and food consumption is measured and recorded weekly for main study animals. Ophthalmoscopic examinations are conducted pretest on all animals and prior to terminal necropsy for main study animals only. Blood samples for clinical pathology evaluations are collected from all main study animals at necropsy. Urine samples are collected on the last day of dosing. Blood samples for determination of the plasma concentrations of the test article are collected from TK animals at designated time points on Days 1 and 28. After the final blood collection, the TK animals are euthanized and the carcasses are discarded without further evaluation. Liver samples for hepatic enzyme induction analysis are collected at terminal necropsy from main study animals. At study termination, necropsy examinations are performed, organ weights are recorded, and prostate and seminal vesicle tissues are microscopically examined. Additional microscopic examination is performed on the left testis from the first five male rats/group at necropsy. The ovary, uterus with cervix, vagina, and mammary gland of females are determined to be target organs.

Following a protocol essentially as described above, systemic exposure ($AUC_{0-24\ hr}$) was highly variable and increased in a less-than-dose-proportional manner with exposure in females exceeding that seen in males. There was no evidence of hepatic microsomal enzyme induction following 28 days of dosing.

There were no unscheduled deaths during the study, and no test article-related clinical signs. Body weight and food consumption were greater among females that received≥150 mg/kg/day relative to controls. These effects did not impact the overall health of the animals and are not considered to be adverse. There were no body weight or food consumption effects evident in males.

There were no test article-related effects on hematology, coagulation, or urinalysis parameters in either sex and no test article-related effects on clinical chemistry parameters in males. Test article-related effects on clinical chemistry parameters in females were limited to increases in alkaline phosphatase at dosages of 150 and 1500 mg/kg/day (1.33 and 1.45-fold increases, respectively), decreases in total protein at dosages of 150 and 1500 mg/kg/day (9% and 10% decreases, respectively), decreases in albumin at dosages of 150 and 1500 mg/kg/day (12% decrease at both dosages) and decreases in globulins at 1500 mg/kg/day only (11% decrease relative to controls). These changes are of minimal magnitude and are not considered to be adverse.

There were no test article-related macroscopic or organ weight changes in either sex and no test article-related microscopic changes in males. Test article-related microscopic changes were present in females in the mammary gland and ovaries at dose levels≥15 mg/kg/day and in the uterus (with cervix) and vagina at dose levels≥150 mg/kg/day. These microscopic changes, which are consistent with a dose-related prolongation of the reproductive cycle in female rats at dose levels≥150 mg/kg/day, are considered to be related to the pharmacology of the test article and are not considered to be adverse.

Based on the results outlined above, the NOAEL for this study is considered to be 1500 mg/kg/day, the highest dose administered. Mean steady-state systemic exposure ($AUC_{0-24\ hr}$) at the NOAEL dose of 1500 mg/kg/day was 102337 ng*hr/mL in males and 216853 ng*hr/mL in females.

Six Month Oral Toxicity Study in Rats

The purpose of this study is to investigate the toxicity and to determine the toxicokinetics of Example 1 in the Sprague- Dawley rat following daily oral gavage for 26 weeks and to assess the reversibility of any findings following a recovery period of 12 weeks. Treated animals receive Example 1 in 5% Vitamin E TPGS, 1% hydroxyethylcellulose, 0.05% Dow Corning Antifoam 1510-US in purified water by oral gavage at daily doses of 15, 150, or 1500 mg/kg/day. Vehicle controls (15 rats/sex in main study and 5 rats/sex in recovery study) are given daily oral gavage dose of 5% Vitamin E TPGS, 1% hydroxyethylcellulose, 0.05% Dow Corning Antifoam 1510-US in purified water. Fifteen males and 15 females are assigned to each treatment main study group. Five males and 5 females are assigned to the recovery study for the vehicle control and 150 mg/kg/day groups. Additional satellite groups of 6 rats/sex for the vehicle control group and 12 rats/sex for the Example 1-treated groups are evaluated for toxicokinetics. All administrations are given in a 15 mL/kg volume.

Following daily oral gavage administration, exposure to Example 1 is highly variable at all doses although non-overlapping mean AUC(0-24 h) values are observed in both males and females between the lowest and highest doses, particularly at Days 91 and 182. Generally, single-dose and multiple dose exposures (Cmax and AUC(0-24 h)) increase less than proportionally from 15 to 1500 mg/kg/day for both males and females. Females exhibit higher exposures than males on all days. On Day 1, female exposure is up to 7-fold higher than the males but this difference decreases to 1 to 3-fold by Day 182. After multiple doses, accumulation of Example 1 is not observed for any dose group up to Day 182.

Following a protocol essentially as described above, there were no mortalities attributed to Example 1 administration during the course of the study. There were no compound-related effects on ophthalmology, or urinalysis parameters.

Example 1—related clinical signs were noted in a dose-dependent fashion in the treated females and consisted of an increase in the incidence of oily fur and a decrease in the incidence of thin cover of the fur. During the first 6 weeks of the recovery period, oily fur was also noted in the females previously treated with 150 mg/kg/day, but was no longer present in these animals in the latter half of the 12-week recovery period. There was no difference in the incidence of thin cover of the fur in the treated and the control females at the end of the recovery period.

In males treated with Example 1, there was a decrease in body weight at all dose levels, reaching −12% when compared to control males at the end of the treatment period. In females, there was an opposite trend, with treated females reaching a 22% higher body weight than concurrent controls at the end of the treatment period. The change in males was still noted at the end of the recovery period, but not in females.

Treated males showed lower food consumption, and treated females generally showed higher food consumption than controls throughout the study correlating with the treatment-related effects on body weight. Food consumption for treated males remained lower than controls during the recovery period, but the magnitude of the difference became negligible at the end of the 12-week period. There was no difference in food consumption of the treated females as compared to the controls during the recovery period.

Administration of Example 1 at dosages≥150 mg/kg/day was associated with increased neutrophil count, absolute reticulocyte count, alkaline phosphatase, potassium and decreased globulins in females. There was an increase in aspartate aminotransferase, alanine aminotransferase, gamma glutamyl transferase, alkaline phosphatase and total bilirubin at 1500 mg/kg/day in males. Minimal decreased total protein and albumin was observed in females at all dose levels. Following a 12-week recovery period, there were no differences in the hematology, clinical biochemistry and urinalysis parameters in rats receiving 150 mg/kg/day indicating reversibility of those findings.

Findings related to treatment with Example 1 were primarily associated with male and female reproductive tissues and were in general attributed to the pharmacology of the molecule. Adverse findings were confined to the testes and occurred in all Example 1-treated groups. There was a decrease in testes and epididymides weight in the 1500 mg/kg/day group, and in individual males given 15 or 150 mg/kg/day that had testicular lesions. Macroscopic findings in male reproductive tissues related to administration of Example 1 were observed in testes and epididymides. Soft and/or small testes and small epididymides were observed in males given≥50 mg/kg/day and a single male given 15 mg/kg/day. Microscopic findings in the testes were seen at all dose levels, were degenerative in nature and included depletion of elongating spermatids, interstitial cell atrophy, and single cell necrosis of spermatocytes. The testicular findings were consistent with decreased circulating luteinizing hormone (LH) resulting in decreased LH signaling at the level of the interstitial cells. Moreover, the decrease in circulating LH levels resulted in decreased testosterone secretion from the testes thereby reducing androgen signaling at the level of the seminiferous tubules. Treatment with Example 1 was also associated with decreased prostate weight observed in males given≥150 mg/kg/day. These reproductive and endocrine changes in males could be related to the pharmacological activity of Example 1 but were not previously identified in a 4-week study. Although consistent with Example 1-related pharmacology, based on magnitude the morphologic findings in the testes seen at all dose levels were considered to be adverse. The effects on male reproductive tissues and LH and testosterone were reversed by the end of the 12-week recovery period.

Administration of Example 1 was associated with decreased weight of ovary and macroscopically small ovaries in females at all dose levels. A decrease in pituitary weight and in circulating levels of LH was observed in females given≥150 mg/kg/day. Microscopic findings were observed in female reproductive tissues related to the administration of Example 1. The microscopic findings in uterus and vagina were observed at dose levels≥150 mg/kg/day while the findings in ovary, and mammary gland were observed at all dose levels. The microscopic findings observed in the female reproductive tissues and the decrease in circulating LH levels were likely related to the pharmacological activity of Example 1. Findings in the female reproductive tissues, including mammary gland, were consistent with those previously reported in the 4-week repeat-dose toxicity study. The female reproductive changes would likely have affected reproductive capability, but not the overall health of the animals. The effects on the female reproductive tissues and LH were reversed by the end of the 12-week recovery period.

Administration of Example 1 was associated with decreased weight of the thymus in females at all dose levels and in males given≥150 mg/kg/day. Macroscopic findings of small thymus were observed in males given 1500 mg/kg/day. Additional microscopic findings related to the administration of Example 1 were observed in liver, spleen, thymus (males), and skin (females), at dose levels≥150 mg/kg/day. Microscopic findings in the skin were observed at all dose levels. All of these changes were no longer present at the end of the 12-week recovery period. There were no other microscopic findings, organ weight changes and macroscopic findings related to the administration of Example 1.

In conclusion, administration of Example 1 by daily oral gavage at dose levels of 0, 15, 150 and 1500 mg/kg/day for 26 weeks was associated with morphologic and hormonal changes in male and female reproductive tissues that were in general attributed to the pharmacology of the molecule, and were reversible after 12 weeks in animals previously treated with 150 mg/kg/day. Adverse findings were confined to the testes and occurred in all Example 1-treated groups. Based on the magnitude of these degenerative testicular changes, a no observable adverse effect level (NOAEL) could not be established in this study and is therefore considered to be <15 mg/kg/day.

Male Fertility and Toxicokinetic Study in Rats

The purpose of this study is to determine the potential adverse effects in the reproductive process resulting from treatment of male rats prior to, and during, the mating period. This includes identification of functional reproductive effects in the male. In addition, a toxicokinetic assessment of plasma levels of Example 1 is performed in satellite animals.

Example 1 is given orally by gavage at doses of 0, 3, 30, and 1000 mg/kg. Male rats (20/group) are treated daily for 10 weeks prior to mating, throughout the 3-week mating period, and continuing through the day prior to euthanasia (for a total of 100 to 101 doses). Female rats are not treated. All animals are observed twice daily for moribundity and mortality. Clinical observations are recorded daily for male rats; body weights and food consumption are recorded for males twice weekly. All males are euthanized 1 day following the last dose administration. Spermatogenic endpoint evaluations conducted on all males include motility and morphology and epididymal sperm concentration. Testes, epididymis, prostate and seminal vesicle/coagulating gland/fluid from all males are weighed and retained. Testes, epididymis, prostate, seminal vesicles and coagulating glands from surviving males are examined microscopically. A laparohysterectomy is performed on Gestation Day 15 for each female with evidence of mating. An additional 3, 18, 18, and 18 males assigned to the toxicokinetic phase are given the compound at doses of 0, 3, 30, and 1000 mg/kg, respectively, and are sampled for toxicokinetic evaluation at appropriate intervals following dose administration on Study Days 0 and 70.

Following daily oral administration of Example 1 to male rats, the time to Cmax is between 2 and 8 hours on Day 0 and 0.5 to 2 hours on Day 70. Mean exposures (measured by AUC0-24 hr) increase between 3 and 30 mg/kg by approximately 7.8-fold and 4.5-fold on Day 0 and 70, respectively, but remain similar between 30 and 1000 mg/kg doses suggesting a plateau in exposure beyond 30 mg/kg. Exposures are generally similar between single and multiple doses.

Following a protocol essentially as described above, one male in the 30 mg/kg group of the toxicokinetic phase and 1 male in the vehicle control group of the main phase were found dead on Study Days 24 and 70, respectively. In the absence of mortality in the 1000 mg/kg group, the death at 30 mg/kg was not considered to be compound-related. At the daily examinations, an increased incidence of red material around 1 or both eyes was noted for 4 males in the 30 mg/kg group and 3 males in the 1000 mg/kg group beginning as early as Study Day 8 and 20, respectively. No other compound-related clinical findings were noted for males in the 3, 30, and 1000 mg/kg groups at the daily examinations or approximately 1 hour following dose administration. Mean body weights, body weight gains, and food consumption were unaffected by compound administration at all dosage levels.

Dose-dependent lower absolute and relative (to body and brain weight) male reproductive organ weights including testes, epididymides (intact and cauda), prostate gland, and seminal vesicles/coagulating gland/accessory fluids were noted in the 30 and 1000 mg/kg groups. The organ weight effects observed in the testes corresponded to histologic changes characterized by atrophy of the interstitial Leydig cells and germinal epithelium. These findings along with reduced populations of mature spermatozoa in the epididymides in both groups and reduced secretions in accessory sex glands noted in the 1000 mg/kg group were considered to be consistent with down regulation of androgen (testosterone) synthesis and/or secretion by Leydig cells or by inhibition of hormone receptors in target organs. The effects noted in the reproductive organs in the 1000 mg/kg group corresponded to reduced reproductive function. In the 30 and 1000 mg/kg groups, the organ weight effects noted in the accessory sex glands (prostate gland, seminal vesicles, and coagulating glands) were considered to be related to the pharmacology of the compound.

Compound-related effects on spermatogenic endpoints were noted in the 1000 mg/kg group. Lower epididymal weights were noted in the 1000 mg/kg group and corresponded to a lower mean epididymal sperm concentration in this group. In addition, a compound-related decrease in the percentage of morphologically normal sperm was observed at 1000 mg/kg as a result of higher numbers of sperm with the head absent or separated from the flagellum. These effects correlated with lower mating, fertility, and copulation indices in the 1000 mg/kg group males. In addition, a slightly longer pre-coital interval was observed in the 1000 mg/kg group compared to the vehicle control group. Spermatogenic endpoints and reproductive performance in the 3 and 30 mg/kg groups were unaffected by compound administration.

Intrauterine survival of the embryos was unaffected by compound administration to males at dose levels of 3, 30, and 1000 mg/kg.

In conclusion, there were no effects on male body weights or food consumption or adverse compound-related clinical findings at any dosage level. Compound-related adverse effects on male reproductive tissues and spermatogenic parameters occurred at 30 and 1000 mg/kg. Decreases in male reproductive organ weights occurred in the 1000 mg/kg and corresponded to effects on epididymal sperm concentration and morphology. In addition, microscopic alterations were observed in the testes, epididymides, prostate, seminal vesicles, and coagulating gland at 1000 mg/kg which corresponded to reductions in mating, fertility, and copulation indices in this group. Although the reduction in reproductive performance generally correlated with histologic changes in male reproductive tissue on a group basis, the correlation on an individual animal basis was not always apparent. In the 30 mg/kg group, decreases in reproductive organ weights and microscopic alterations in the testes and epididymides were noted. No corresponding effects on reproductive function were noted at 30 mg/kg which suggests that the pharmacological signal while present was not great enough to affect functional reproduction. Based on these findings, the NOAEL for male reproductive toxicity and male systemic toxicity was 3 mg/kg. A dose level of 3 mg/kg corresponds to an exposure (AUC0-24 hours) value on Study Day 70 of 10,954 ng·hrs/mL.

Four Week Oral Toxicity Study in Dogs

This study is conducted to evaluate the potential toxicity and toxicokinetics of Example 1, a selective androgen receptormodulator (SARM), in dogs after twice daily oral capsule administration for 4 weeks. Three treatment groups of three male and three female beagle dogs are administered the test article at respective dose levels of 6, 60, or 300 mg/kg/day. One additional group of three animals/sex serves as the control and receives the vehicle, 80% PEG 3350/20% Vitamin E TPGS (v/v) via oral capsule. The test article or vehicle is administered to all groups via oral capsule, twice a day for 28 consecutive days, at a dose volume of 1.5 mL/kg/dose.

Observations for mortality, morbidity, injury, and the availability of food and water are conducted twice daily for all animals. Detailed clinical observations are conducted weekly. Body weights are measured and recorded the day after receipt, prior to randomization, and weekly during the study. Food consumption is measured and recorded weekly. Ophthalmoscopic examinations are conducted pretest and prior to the terminal necropsy. Physical examinations are conducted pretest. Neurological examinations are conducted during Weeks 1 and 4. ECG examinations are conducted twice prior to the initiation of dosing and prior to and approximately 2 hours (±15 minutes) after the morning test article administration on Days 3 and 26. Blood samples are collected twice pretest, and blood and urine samples for clinical pathology evaluations are collected from all animals prior to the terminal necropsy. Blood samples for determination of the plasma concentrations of the test article are collected from all animals at designated time points on Days 1 and 28. The toxicokinetic parameters are determined for the test article from concentration-time data in the test species. At study termination, necropsy examinations are performed, organ weights are recorded, and testes, epididymis, and prostates are microscopically examined. The potential of Example 1 to induce cytochromes P450 is determined by analyzing frozen liver samples for total cytochrome P450 content.

Following a protocol essentially as described above, no measurable (<1 ng/mL) concentrations of Example 1 were found in any of the plasma samples from the control animals. No differences in Example 1 plasma concentrations were noted between males and females indicating no gender effect on exposure. Exposure of Example 1 increased in a less than dose proportional manner in animals given 6 and 60 mg/kg/day and appeared to reach a plateau at 60 mg/kg/day, as plasma concentrations were similar to those at 300 mg/kg/day.

52 Week Toxicity and Toxicokinetic Study in Dogs

The purpose of this study is to evaluate the toxicity and determine the toxicokinetics of the test article, Example 1, when administered daily by capsule to dogs for at least 52 weeks and to assess the reversibility, persistence, or delayed occurrence of any effects after a 13-week recovery.

Male and female purebred beagle dogs are assigned to groups, and doses are administered according to Table 9 via oral capsules containing 1 ml/kg of 0 [1% (w/v) carboxymethylcellulose sodium (low viscosity/25-50 cps), 0.5% (w/v) sodium lauryl sulfate and 0.05% (v/v) Dow Corning® Antifoam 1510-US in reverse osmosis water] 3, 10, or 100 mg Example 1/kg of bodyweight. All animals receive the same number of capsules, and Group 1 animals receive capsules containing vehicle control article only. Three animals per sex from Groups 1 and 4 are designated as recovery animals.

TABLE 9

| Group | Number of Animals Male | Number of Animals Female | Dose Level (mg Example 1/kg) | Dose Concentration (mg Example 1/kg) |
|---|---|---|---|---|
| 1 (Control) | 7 | 7 | 0 | 0 |
| 2 (Low) | 4 | 4 | 3 | 3 |
| 3 (Mid) | 4 | 4 | 10 | 10 |
| 4 (High) | 7 | 7 | 100 | 100 |

Assessment of toxicity is based on mortality, clinical signs, body weight and body weight change, food consumption, ophthalmic and neurologic evaluations, ECG measurements, hormone analysis (testosterone, progesterone, luteinizing hormone, and follicle stimulating hormone), semen evaluation (ejaculate volume and sperm number, density, morphology, and motility), and clinical and anatomic pathology. Blood samples are collected for exploratory metabolite analysis and toxicokinetic evaluations.

Following a protocol essentially as described above, systemic exposure to Example 1 increased with the increase in dose level from 3 to 100 mg/kg. The increases in mean Cmax and $AUC_{0-24\ hr}$ were generally less than dose proportional. No consistent sex-related differences were observed in the toxicokinetic parameters. Accumulation of Example 1 was observed after multiple dosing of Example 1 in dogs.

All animals survived until the scheduled sacrifice. Compound-related clinical signs were increased observations of lacrimation in animals given >3 mg/kg and reduced or absent estrous cycling in females given >3 mg/kg.

No toxicologically important differences were noted in mean body weights, body weight gains, and food consumption. No ophthalmic or neurologic abnormalities occurred.

Prolonged QT interval and corrected QT (QTc) interval was noted predose and 2 hours postdose on Days 3, 86, and 359 of the dosing phase in combined sexes given 100 mg/kg. The magnitude of the increase in mean QTc interval in combined sexes given 100 mg/kg across all dosing phase intervals ranged from 14 to 21 msec (6 to 9%) over mean values for control animals. No compound-related changes on QT or QTc interval were noted on Day 88 of the recovery phase in combined sexes given 100 mg/kg or on Days 3, 86, or 359 of the dosing phase in animals given 3 or 10 mg/kg. No Example 1-related changes in PR interval, QRS duration, RR interval, or heart rate were observed on Day 3, 86, or 359 of the dosing phase in animals given 3, 10, or 100 mg/kg or on Day 88 of the recovery phase in animals given 100 mg/kg. No rhythm abnormalities or qualitative ECG changes were attributed to Example 1 during qualitative assessment of the electrocardiograms.

Example 1—related, dose-dependent decreases in total sperm count occurred during the dosing phase for males at all dose levels and were attributed to decreases in ejaculate weight. At the Week 52 assessments (Days 355 and 360 of the dosing phase), total sperm count relative to controls was decreased >55, >50, and >91% for males administered 3, 10, or 100 mg/kg, respectively. Effects on total sperm count completely reversed during the recovery phase. No Example 1-related effects on mean sperm density, motility, or morphology were noted for any group.

Hormonal changes were noted in males and females given>3 mg/kg. The changes were consistent with the pharmacology of the test article and correlated with microscopic changes. In males, reductions in testosterone and increases in LH were observed. Increased LH and decreased progesterone in the female were consistent with anestrus and reduction of corpora lutea noted microscopically. Hormonal levels returned to control levels during the recovery phase.

Compound-related clinical pathology effects were limited to minimally to mildly increased alanine aminotransferase activity for males and females at all dose levels (females given 100 mg/kg were most affected) and minimally to moderately decreased cholesterol for males and females given 3 or 10 mg/kg (animals given 3 mg/kg were most affected). The effect on alanine aminotransferase activity at 100 mg/kg exhibited reversibility following the recovery phase. Reversibility of the effect on cholesterol concentration at 3 and 10 mg/kg could not be assessed because no animals at these dose levels were in the recovery phase. Neither of these effects was associated with correlative microscopic findings.

Pharmacologically expected compound-related morphologic changes were noted in reproductive tissues of males and females. Compound-related and reversible decreased prostate, epididymis, and liver/gall bladder weights occurred in males, which, with the exception of the liver/gall bladder changes, correlated with microscopic findings. In the prostate gland, males given>3 mg/kg had reversible prostate gland acinar epithelial atrophy. Males given>3 mg/kg had reversible decreased ductular diameter of the cauda (tail) of the epididymis, and males given 100 mg/kg had reversible epididymal ductular epithelial atrophy. Females given>3 mg/kg had decreased/absent corpora lutea with anestrus cycle stage in the ovary. This change was generally accompanied by a lack of lobular development in the mammary gland as well as expected responses of secondary reproductive tissues to anestrus: the uterus, cervix, vagina, and mammary gland, had stage-appropriate features of atrophy commensurate with prolonged anestrus.

Collectively, these findings in females are consistent with compound-related disruption of normal reproductive cycling. In the recovery phase, 2/3 females given 100 mg/kg had diestrus reproductive cycle stage and lobular mammary development, indicating a return to normal cyclic activity, although no clinical evidence of reproductive cycling was noted during the recovery phase.

Additionally, compound-related and reversible microscopic findings were observed in the adrenal gland and skin/subcutis. In the adrenal gland, males given>10 mg/kg and females given 100 mg/kg had decreased vacuolation of the zona fasciculata and reticularis. In the skin, decreased sebaceous gland vacuolation was noted in animals given>3 mg/kg.

In summary, daily administration of Example 1 by capsule to dogs for 52 weeks at a dose level of 3, 10, or 100 mg/kg resulted in no adverse compound-related findings. Changes in reproductive function occurred in males (decreased sperm count and ejaculate volume) and females (reduced/absent estrous cycling) of all Example 1-treated groups and correlated with microscopic findings. These changes do not affect the overall health of the animals; are consistent with the pharmacologic action of the test article; and are reversible. Therefore, the NOAEL is 100 mg/kg. After 361 days of dosing, a dose of 100 mg/kg corresponded to mean Cmax values of 1496 and 1885 ng/mL and $AUC_{0-24\,h}$ values of 22582 and 31505 ng·hr/mL in males and females, respectively.

TABLE 10

Summary of Prostate Findings from Rats and Dogs Treated with Example 1

RATS

| | Treatment Duration (months) | | | | | | | | |
|---|---|---|---|---|---|---|---|---|---|
| | $1^a$ | | | $6^a$ | | | Male Fertility (3 mos)$^a$ | | |
| Dose (mg/kg/day) | 15 | 150 | 1500 | 15 | 150 | 1500 | 3 | 30 | 1000 |
| Prostate weight (mean % decrease) | — | — | — | — | ↓ 30% | ↓ 34% | — | ↓ 23% | ↓ 39% |
| Prostate atrophy (no. affected/no. examined) | — | — | — | — | — | 4/15 | — | — | — |
| Male group mean $AUC_{0-24\,hr}$ near termination (ng * hr/mL) | 35733 | 72283 | 102337 | 15902 | 34132 | 82690 | 10954 | 49734 | 56009 |

— No effect observed
$^a$Vehicle 5% Vitamin E TPGS, 1% hydroxyethylcellulose, 0.05% DC Antifoam 1510-US in purified water

DOGS

| | Treatment Duration (months) | | | | | | | | |
|---|---|---|---|---|---|---|---|---|---|
| | $1^a$ | | | $6^a$ | | | $12^b$ | | |
| Dose (mg/kg/day) | 3 | 30 | 150 | 3 | 30 | 300 | 3 | 10 | 100 |
| Prostate weight (mean % decrease) | — | — | — | ↓ 63% | ↓ 66% | ↓ 75% | ↓60% | ↓62% | ↓ 80% |
| Prostate atrophy (no. affected/no. examined) | — | — | 1/4 | 4/4 | 4/4 | 4/4 | 2/4 | 3/4 | 4/4 |
| Male group mean $AUC_{0-24\,hr}$ near termination (ng * hr/mL) | 17984 | 61674 | 46528 | 6492 | 44448 | 53032 | 3621 | 13408 | 22582 |

— No effect observed
$^a$Vehicle 80% PEG 1350, 20% Vitamin E TPGS (v/v)
$^b$Vehicle 1% (w/v) carboxymethylcellulose sodium, 0.5% (w/v) sodium lauryl sulfate, 0.05% (v/v) Dow Corning® Antifoam 1510-US in reverse osmosis water Treatment with Example 1 to intact rats or dogs for the periods ranging from 1 to 12 months results in a significant decrease in prostate size which further indicates that it does not accrue androgenic risk of prostate hyperplasia over time.

In Vivo Study to Explore any Direct Antagonist Effect of Example 1 in the Presence of TE A total of 36 orchidectomized (ORX) and 6 sham-operated Wistar male rats are used (orchidectomized at 8 weeks of age and allowed to waste for 4 weeks). The rats are maintained on a 12 hr light/dark cycle at 22° C. with ad lib access to food (TD 5001 with 0.95% Ca and 0.67% P, Teklad, Madison, Wis.) and water. Rats are randomized and placed into treatment groups (n=6) based on body weight. Route of administration for all groups except TE is oral. TE is administered subcutaneously. At the end of 8 weeks of daily dosing, rats are euthanized, weighed & tissue harvested. Levator ani, prostates, and seminal vesicles are collected from each animal. Results are plotted as means±SE.

Means Comparisons of Seminal Vesicle Wet Weights Comparisons with a Control Using Dunnett's Method Control Group = d-ORX + TE, 1 mg/kg/d

| |d| | Alpha |
|---|---|
| 2.69715 | 0.05 |

TABLE 11

| Group No | Group | Abs(Dif) – LSD | p-Value |
|---|---|---|---|
| 1 | Sham | 0.979 | <.0001 |
| 2 | ORX + TE, 1 mg/kg/d | -0.52 | 1.0000 |
| 3 | ORX + TE, 1 mg/kg/d + Example 1, 3 mg/kg/d | -0.34 | 0.8628 |
| 4 | ORX + TE, 1 mg/kg/d + Example 1, 10 mg/kg/d | 0.078 | 0.0187 |
| 5 | ORX + TE, 1 mg/kg/d + Example 1, 30 mg/kg/d | 0.536 | <.0001 |
| 6 | ORX + Example 1, 10 mg/kg/d | 1.411 | <.0001 |
| 7 | ORX, Vehicle | 1.422 | <.0001 |

Positive values show pairs of means that are significantly different.

Figure 5:
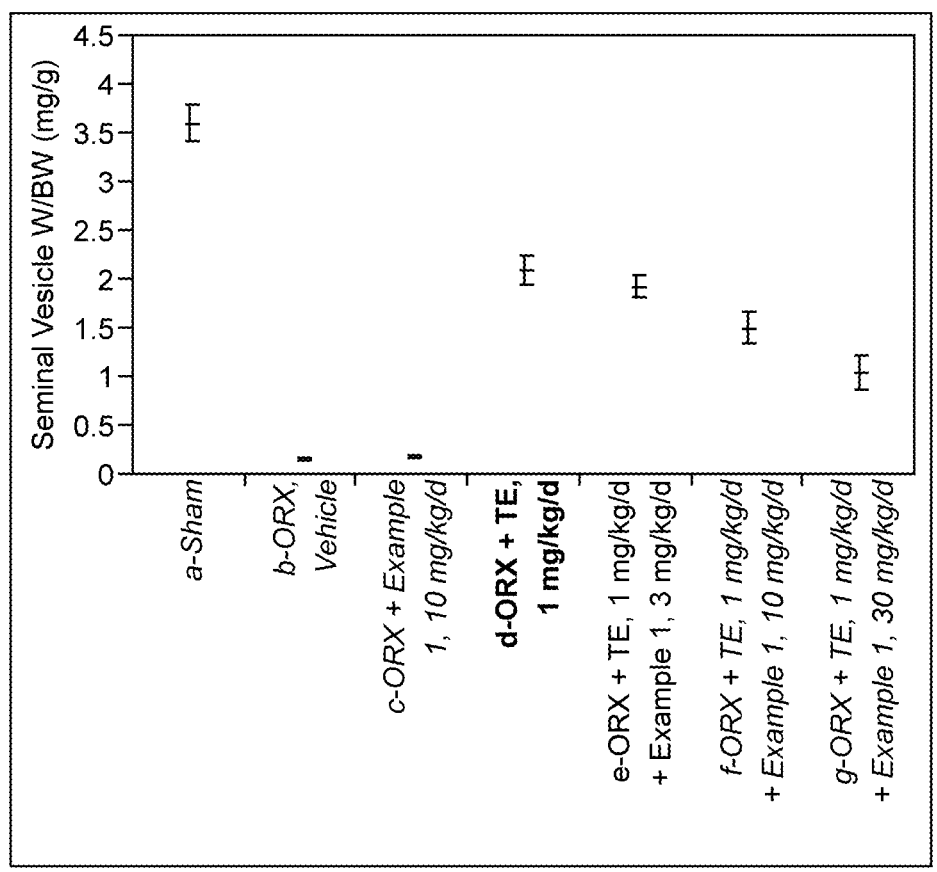
FIG. 5 illustrates that the combination with TE (1 mg/Kg-day) and various doses of Example 1 suggest a trend in decreasing seminal vesicle wet weight in milligrams normalized to body weight in grams, which is induced by TE alone.

Combination with Testosterone Enanthate (1 mg/Kg-day) and various doses of Example 1 suggest a trend in decreasing seminal vesicle wet weight in mg normalized to body weight in gms, which is induced by TE alone as shown in FIG. 5 and Table 11.

Means Comparisons of Prostate Weights Comparisons with a Control Using Dunnett's Method Control Group = d-ORX + TE, 1 mg/kg/d

| |d| | Alpha |
|---|---|
| 2.69715 | 0.05 |

TABLE 12

| Group No | Group | Abs(Dif) – LSD | p-Value |
|---|---|---|---|
| 1 | Sham | 0.509 | <.0001* |
| 2 | ORX + TE, 1 mg/kg/d | -0.15 | 1.0000 |
| 3 | ORX + TE, 1 mg/kg/d + Example 1, 3 mg/kg/d | -0.11 | 0.9774 |
| 4 | ORX + TE, 1 mg/kg/d + Example 1, 30 mg/kg/d | 0.025 | 0.0167* |
| 5 | ORX + TE, 1 mg/kg/d + Example 1, 10 mg/kg/d | 0.036 | 0.0099* |
| 6 | ORX, Vehicle | 0.356 | <.0001* |
| 7 | ORX + Example 1, 10 mg/kg/d | 0.357 | <.0001* |

Figure 6:
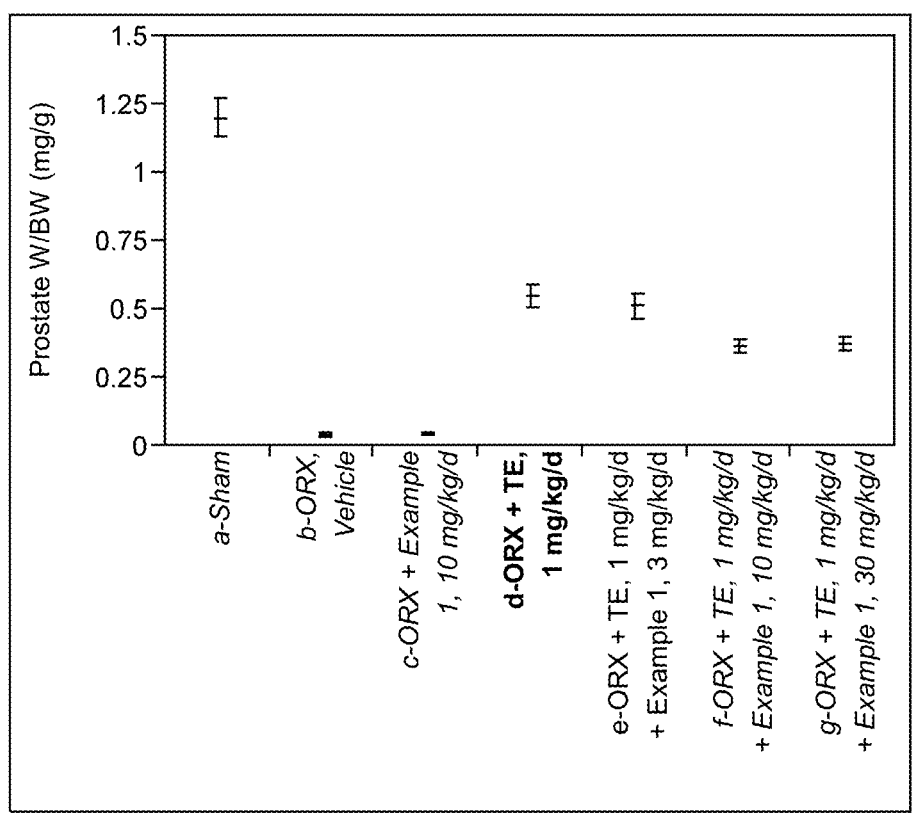
FIG. 6 illustrates that the co-treatment of Example 1 to SD rats along with 1 mg/Kg TE results in a dose-dependent decrease in prostate wet weight in milligrams normalized to body weight in grams.

Positive values show pairs of means that are significantly different than TE alone group Co-treatment of Example 1 to SD rats along with 1 mg/Kg TE results in a dose-dependent decrease in prostate wet weight in mgs normalized to body weight in grams as shown in FIG. 6 and Table 12.

TABLE 13

| | hAR Ki (nM) | LnCAP Gene Expression EC50 (nM) | | |
|---|---|---|---|---|
| | | PSA | AR | CLUSTERIN |
| R1881 | 0.38 | 0.034 | 0.035 | 0.37 |
| Example 1 | 1.95 | 2.64 | 1.64 | >100 |

Comparisons of Example 1 with the synthetic Testosterone R1881, show that in vitro using human prostate cancer cells Example 1 is less androgenic than R1881. In contrast the biochemical binding affinity to the human Androgen receptor (hAr; Ki in nM) is only modestly reduced.

Phase Ia Study in Healthy Volunteers

This Phase 1 study is a randomized, placebo-controlled, double-blind, single-dose, incomplete-crossover, dose-escalation design, conducted in 3 dosing cohorts consisting of healthy men and postmenopausal women. Thirty subjects (10 per cohort) are randomly assigned to each dosing cohort.

During both dosing periods, subjects are admitted to the clinical research unit (CRU) for overnight stays. Subjects are dosed orally after breakfast on Day 1 and remain at the CRU for approximately 24 hours after dosing. Within each cohort, the washout period between dosing periods ranges from 14 to 45 days. A study discharge visit occurs approximately 5 days after the last dose, Period 2. The appropriateness of dose escalation is determined by safety measurements at each step of the escalation. A subject-investigator double blinded crossover design is used for this study to provide between-subject data for all safety and tolerability measurements. This design facilitates objective assessment of AEs.

A protocol essentially as described above was followed. As a result of the incomplete crossover design, approximately 50% of subjects received a single dose of Example 1 and a placebo dose in order to enhance detection of significant safety or tolerability signals. Approximately 50% of the subjects received Example 1 at 2 dose levels, which allowed for a within subject analysis of the dose-dependency of PK parameters and other endpoints. A minimum 5-day dosing interval period was chosen to minimize carryover effects between treatment periods.

The planned dose range for this study was from 5 to 1000 mg of Example 1 and was based on in vivo efficacy in rat, using the assumption that the exposure required to produce an 80% bone effect (average of mid-shaft load and femoral neck load) in rat is the same as the exposure required in human. Based on the allometrically predicted human clearance (33 Uh, 90% confidence interval [CI]: 24 to 46 Uh) and bioavailability (49%), such a response in humans is expected to occur at doses of around 71 mg/day (90% CI: 29 to 321 mg/day).

Figure 7:
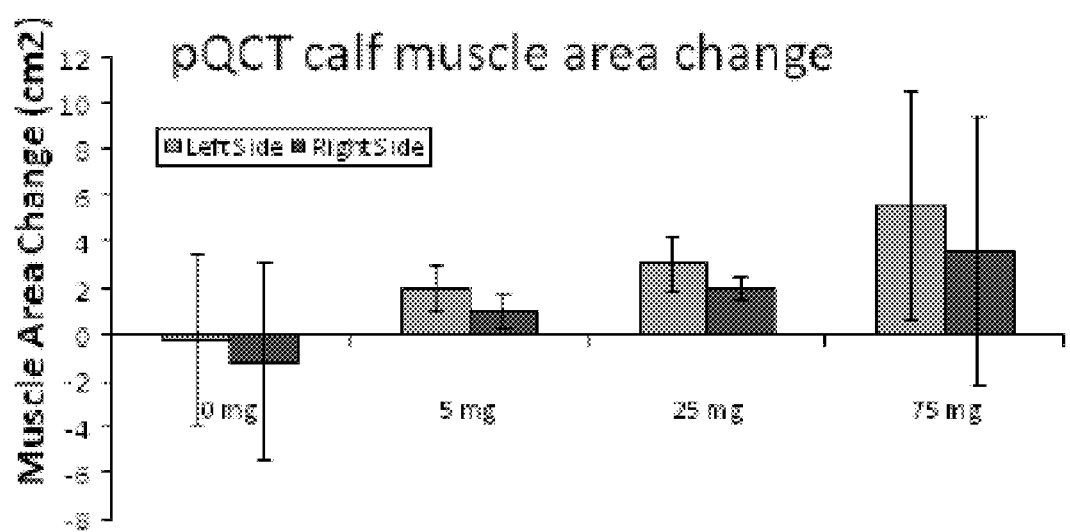
FIG. 7 illustrates an increase in calf muscle area as measured by peripheral Computer Tomography based imaging at the gastrocnemius bundle (calf muscle area) after administration of Example 1 to healthy human volunteers.

These data demonstrate an increase in calf muscle area as measured by peripheral Computer Tomography based imaging at the gastrocnemius bundle (calf muscle area) after administration of Example 1 to healthy human volunteers as shown in FIG. 7.

TABLE 14

Summary of Change from Baseline for Lean Muscle by Dose at Day 28 - Males

| Treatment Group | n | LS Mean[95% CI] | Comparison to Placebo Difference[95% CI] [Pvalue] |
|---|---|---|---|
| Placebo | 7 | −873.45 [−2318.30, 571.39] | |
| 1 mg LY | 7 | 675.52 [−762.14, 2113.18] | 1548.97 [−491.08, 3589.02] [.130] |
| 5 mg LY | 8 | 587.66 [−757.35, 1932.67] | 1461.11 [−510.41, 3432.63] [.139] |
| 15 mg LY | 2 | 2329.08 [−453.16, 5111.33] | 3202.54 [100.93, 6304.14] [.044] |
| 25 mg LY | 2 | 956.18 [−1773.88, 3686.23] | 1829.63 [−1281.37, 4940.62] [.236] |
| 75 mg LY | 4 | −1557.21 [−3500.36, 385.94] | −683.76 [−3129.22, 1761.70] [.569] |

The mixed model: chg = base dose ddfm = kr;
Unit = g
Program: Home/lillyce/prd/ly2452473/i2n_mc_gpbc/final/programs_stat/gpbc_smim_update.sas

TABLE 15

Summary of Change from Baseline for Lean Muscle by Dose at Day 28 - Females

| Treatment Group | n | LS Mean[95% CI] | Comparison to Placebo Difference[95% CI] [Pvalue] |
|---|---|---|---|
| Placebo | 3 | −742.27 [−3136.75, 1652.21] | |
| 5 mg LY | 3 | 1555.95 [−1092.94, 4204.84] | 2298.22 [−2183.05, 6779.50] [.271] |
| 15 mg LY | 2 | 2919.58 [−679.64, 6518.81] | 3661.85 [−1742.10, 9065.81] [.157] |
| 25 mg LY | 4 | 1482.24 [−1013.85, 3978.33] | 2224.51 [48.22, 4400.81] [.046] |
| 75 mg LY | 2 | 1583.65 [−506.14, 3673.45] | 2325.92 [−1178.94, 5830.78] [.164] |

Figure 8:
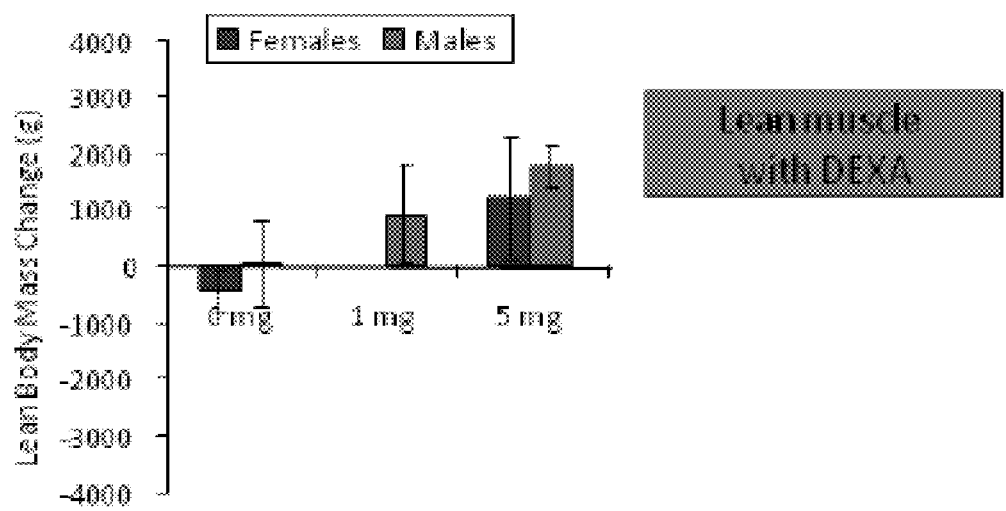
FIG. 8 illustrates an increase in whole body lean muscle mass after administration of Example 1 to healthy human volunteers as measured by DEXA. The effect in males (blue bar) at the 5 mg dose level is statistically significant compared to the 0 mg placebo dose, using a Dunnett's test ($p<0.05$).

The mixed model: chg = base dose ddfm = kr;
Unit = g
Program: Home/lillyce/prd/ly2452473/i2n_mc_gpbc/final/programs_stat/gpbc_smim_update.sas These data demonstrate an increase in whole body lean muscle mass after administration of Example 1 to healthy human volunteers as measured by DEXA. The effect in males (blue bar) at the 5 mg dose level is statistically significant compared to the 0 mg placebo dose, using a Dunnett's test (p<0.05) as shown in FIG. 8 and Tables 14 and 15.

TABLE 16

Summary of Change from Baseline for Prostate Specific Antigen by Dose and Time - Males

| Treatment Group | Tine/day | n | LS Mean[95% CI] | Comparison to Placebo Difference[95% CI] [Pvalue] |
|---|---|---|---|---|
| Placebo | 14 | 7 | 0.04 [−0.11, 0.20] | |
|  | 28 | 7 | 0.05 [−0.11, 0.20] | |
|  | 35 | 7 | 0.03 [−0.13, 0.18] | |
| 1 mg LY | 14 | 7 | −0.06 [−0.21, 0.09] | −0.10 [−0.31, 0.12] [.362] |
|  | 28 | 7 | −0.05 [−0.20, 0.10] | −0.09 [−0.31, 0.12] [.390] |
|  | 35 | 7 | 0.02 [−0.13, 0.17] | −0.01 [−0.22, 0.21] [.940] |
| 5 mg LY | 14 | 8 | 0.20 [0.06, 0.34] | 0.16 [−0.05, 0.37] [.140] |
|  | 28 | 8 | −0.00 [−0.15, 0.14] | −0.05 [−0.26, 0.16] [.635] |
|  | 35 | 8 | 0.20 [0.06, 0.34] | 0.17 [−0.04, 0.39] [.106] |

TABLE 16-continued

Summary of Change from Baseline for Prostate
Specific Antigen by Dose and Time - Males

| Treatment Group | Tine/day | n | LS Mean[95% CI] | Comparison to Placebo Difference[95% CI] [Pvalue] |
|---|---|---|---|---|
| 15 mg LY | 14 | 2 | −0.11 [−0.40, 0.17] | −0.16 [−0.48, 0.16] [.331] |
|  | 28 | 2 | −0.27 [−0.55, 0.01] | −0.31 [−0.63, 0.01] [.055] |
|  | 35 | 2 | 0.25 [−0.03, 0.53] | 0.22 [−0.10, 0.54] [.174] |
| 25 mg LY | 14 | 2 | −0.15 [−0.43, 0.13] | −0.19 [−0.51, 0.13] [.243] |
|  | 28 | 2 | −0.22 [−0.50, 0.06] | −0.27 [−0.59, 0.05] [.097] |
|  | 35 | 2 | −0.14 [−0.42, 0.14] | −0.17 [−0.49, 0.15] [.295] |
| 75 mg LY | 14 | 4 | −0.13 [−0.33, 0.07] | −0.17 [−0.43, 0.09] [.185] |
|  | 28 | 3 | 0.07 [−0.15, 0.30] | 0.03 [−0.25, 0.30] [.851] |
|  | 35 | 4 | 0.03 [−0.17, 0.23] | 0.00 [−0.26, 0.26] [.997] |

Figure 9:
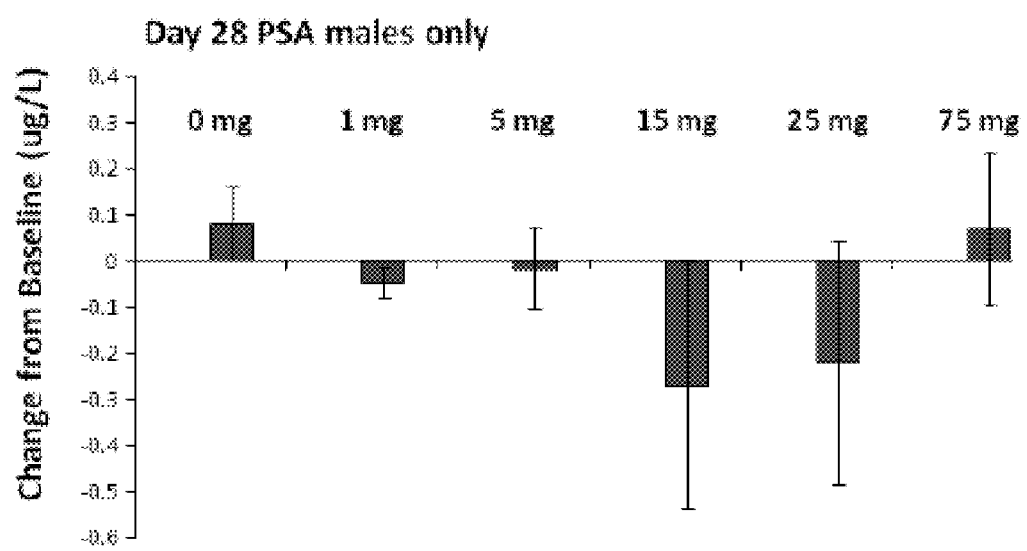
FIG. 9 illustrates that there are no significant changes from baseline in prostate-specific antigen (SPA) levels when compared with placebo at any time point or any dose of Example 1.

The mixed model: chg = base dose VISITDY dose*VISITDY/ddfm = kr; repeated VISITDY/subject = subject type = cs;
Unit = ug/L
Program: Home/lillyce/prd/ly2452473/i2n_mc_gpbc/final/programs_stat/gpcc_smlab_update.sas These data of Figure demonstrate that there are no significant changes from baseline in prostate-specific antigen (SPA) levels when compared with placebo at any time point or any dose of Example 1 as shown in FIG. 9 and Table 16.

Phase Ib Study of Healthy Volunteers

This is a Phase 1, randomized, placebo-controlled, subject- and investigator-blind, multiple-dose, dose-escalation, parallel study of Example 1 in healthy subjects. This study is conducted in 6 treatment groups, and subjects were randomized to receive daily doses of either Example 1 or placebo for 4 weeks. An evaluation of safety and tolerability is performed prior to each dose escalation. Key inclusion/exclusion criteria for this study are that the subjects be healthy males or healthy postmenopausal females, between the ages of 30 and 80 years, inclusive; with a body mass index (BMI) between 18 and 32 kg/m2, inclusive.

Subjects are entered into the study and randomized after screening. On days 1 and 29 subjects are inpatient on the Clinical Research Unit (CRU). On Days 1, 2, and 28, subjects are dosed orally after breakfast. All safety labs are collected prior to breakfast and following an overnight fast of at least 12 hours.

Following Day 1, subjects are discharged on Day 2 following scheduled procedures, breakfast, and dosing (approximately 24 hours following Day 1 dose). Following Day 28, subjects are discharged on Day 29 following scheduled procedures (approximately 24 hours following Day 28 dose).

Figure 10:
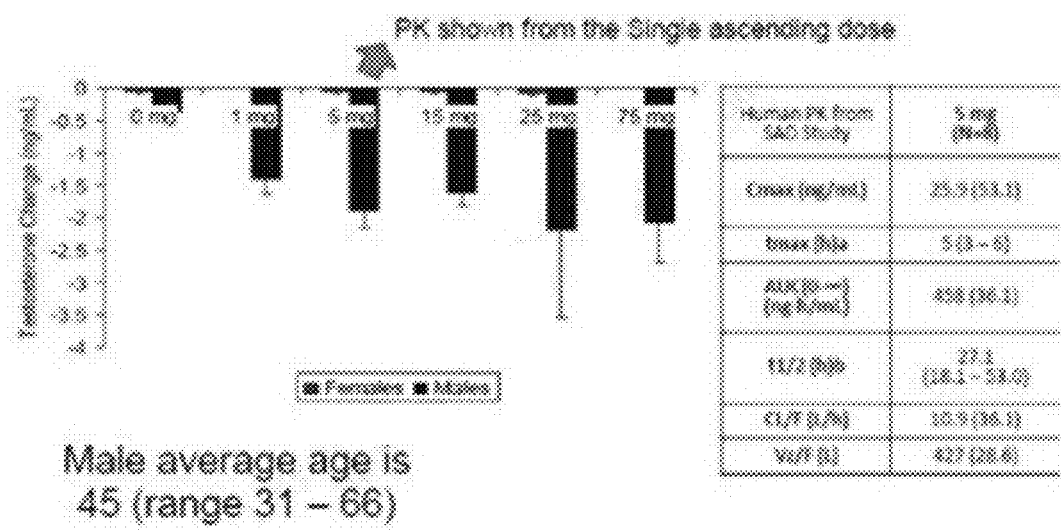
FIG. 10 illustrates a decrease in serum testosterone levels after administration of Example 1 to eugonadal healthy human volunteers. The decrease after treatment is more pronounced in males given their relatively higher serum testosterone levels. The table on the right reflects the exposure assessment after the Ph1a study at the 5 mg dose.

These data demonstrate a decrease in serum testosterone levels after administration of Example 1 to eugonadal healthy human volunteers. The decrease after treatment is more pronounced in males given their relatively higher serum testosterone levels. The table on the right reflects the exposure assessment after the PhIa study at the 5 mg dose as shown in FIG. 10.

TABLE 17

Summary of Change from Baseline for Procollagen Type
I N Propeptide (P1NP) by Does and Time - Males

| Treatment Group | Time/day | n | LS Mean[95% CI] | Comparison to Placebo Difference[95% CI] [Pvalue] |
|---|---|---|---|---|
| Placebo | 14 | 7 | −1.15 [−7.55, 5.24] | |
|  | 28 | 7 | −1.32 [−7.72, 5.07] | |
|  | 35 | 7 | −3.44 [−9.83, 2.96] | |
| 1 mg LY | 14 | 7 | −3.55 [−9.70, 2.59] | −2.40 [−11.09, 6.29] [.580] |
|  | 28 | 7 | 0.16 [−5.98, 6.30] | 1.49 [−7.20, 10.17] [.731] |
|  | 35 | 7 | −5.70 [−11.84, 0.45] | −2.26 [−10.94, 6.43] [.602] |
| 5 mg LY | 14 | 8 | 2.11 [−3.65, 7.88] | 3.27 [−5.56, 12.09] [.458] |
|  | 28 | 8 | 2.88 [−2.90, 8.55] | 4.20 [−4.62, 13.02] [.341] |
|  | 35 | 8 | −2.31 [−8.08, 3.46] | 1.13 [−7.70, 9.95] [.797] |
| 15 mg LY | 14 | 2 | 1.34 [−10.64, 13.32] | 2.49 [−11.62, 16.60] [.723] |
|  | 28 | 2 | 2.09 [−9.89, 14.07] | 3.41 [−10.70, 17.52] [.627] |
|  | 35 | 2 | −3.41 [−15.39, 8.57] | 0.03 [−14.08, 14.14] [.997] |
| 25 mg LY | 14 | 2 | −2.07 [−13.70, 9.56] | −0.92 [−14.54, 12.70] [.892] |
|  | 28 | 2 | 1.43 [−10.20, 13.06] | 2.75 [−10.86, 16.37] [.685] |
|  | 35 | 2 | −2.97 [−14.60, 8.66] | 0.47 [−13.15, 14.08] [.945] |
| 75 mg LY | 14 | 4 | −4.96 [−13.02, 3.09] | −3.81 [−14.06, 6.44] [.457] |
|  | 28 | 3 | 1.48 [−7.27, 10.24] | 2.81 [−8.02, 13.64] [.604] |
|  | 35 | 4 | −1.09 [−9.15, 6.97] | 2.35 [−7.90, 12.60] [.646] |

Figure 11:
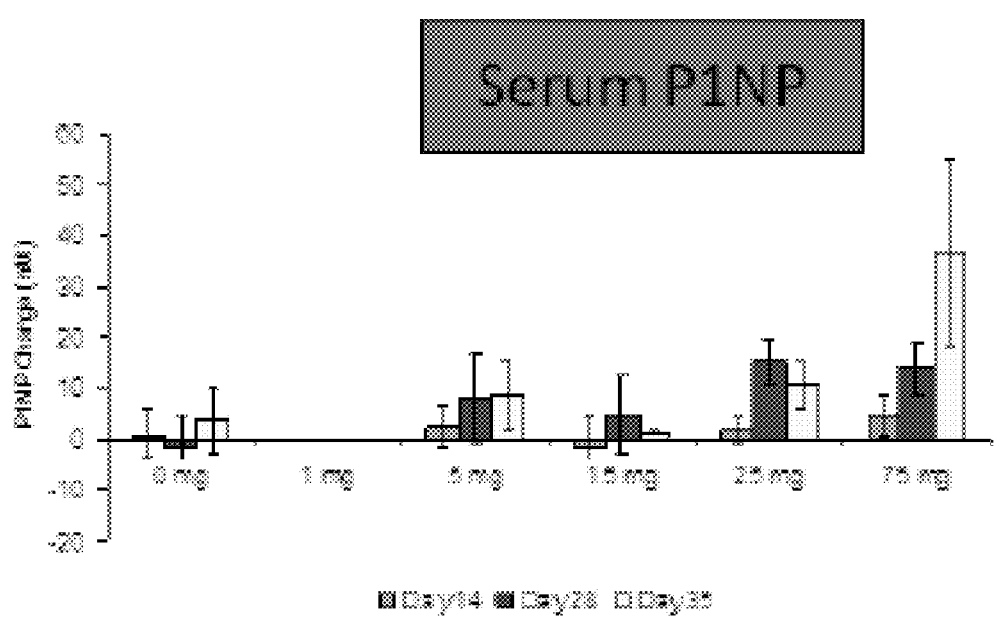
FIG. 11 illustrates a positive exposure-response relationship for N-terminal propeptide of procollagen type 1 (P1NP), a biomarker for bone anabolism, after administration of Example 1 to eugonadal healthy human volunteers.

The mixed model: chg = base dose VISITDY dose*VISITDY/ddfm = kr; repeated VISITDY/subject = subject type = cs;
Unit = ug/L
Program: Home/lillyce/prd/ly2452473/i2n_mc_gpbc/final/programs_stat/gpbc_smlab_update.sas These data demonstrate a positive exposure-response relationship for N-terminal propeptide of procollagen type 1 (P1NP), a biomarker for bone anabolism, after administration of Example 1 to eugonadal healthy human volunteers as shown in FIG. 11 and Table 16.

What is claimed is:

1. A process for the preparation of the compound of Formula I

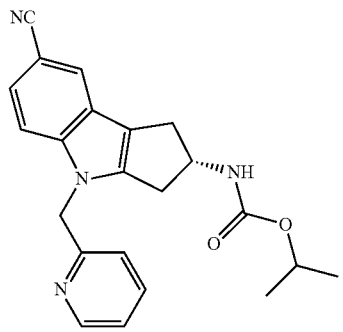
(Formula I)

comprising the steps of:
(a) reacting Zn(CN)₂ with the compound of Formula II, thereby forming the compound of Formula III

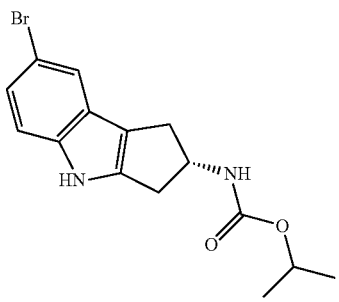
(Formula II)

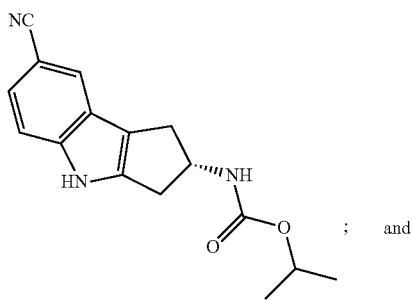
(Formula III)

; and (b) forming the compound of Formula I by reacting the compound of Formula III with the compound of Formula IV

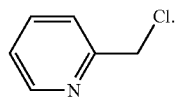
(Formula IV)

2. The process of claim 1, wherein the reaction of the compound of Formula II with Zn(CN)₂ to form a compound of Formula III comprises:
(i) reacting the compound of Formula II with Zn(CN)₂, Zn(OAc)₂, Zn, and Pd(dppf)₂Cl₂·CH₂Cl₂ in DMAc to form a compound of Formula III in solution;
(ii) adding water to precipitate and isolate the compound of Formula III from the solution;
(iii) dissolving the precipitated isolate of the compound of Formula III in a mixture of MTBE and acetone to form a slurry;
(iv) filtering the slurry to form a filtrate having a compound of Formula III; and
(v) treating the filtrate having a compound of Formula III with charcoal, MgSO₄, and FLORISIL™.

3. The process of claim 2, wherein the compound of Formula III is crystalized in the heptane.

4. The process of claim 1, wherein a substantially pure form of a compound of Formula I is produced by a process which comprises the steps of:
(i) reacting the compound of Formula III with 2-picolyl chloride hydrochloride and K₂CO₃ in DMAC to give a compound of Formula I in solution; and
(ii) isolating the compound of Formula I by adding water to the solution formed in step (i) and filtering.

5. The process of claim 4, additionally comprising the further step of:
(iii) recrystallizing the filtered isolate in EtOH to produce a substantially pure crystalline form of a compound of Formula I.

6. The process of claim 5, wherein the filtered isolate is recrystallized at least three times in EtOH to produce a substantially pure crystalline form of a compound of Formula I.

7. The process of claim 6, wherein said substantially pure crystalline form of a compound of Formula I comprises less than 15% by weight of impurities.

* * * * *